(12) United States Patent
Venn-Watson

(10) Patent No.: US 10,307,388 B2
(45) Date of Patent: Jun. 4, 2019

(54) COMPOSITIONS AND METHODS FOR DIAGNOSIS AND TREATMENT OF INFLAMMATION

(71) Applicant: The United States of America as represented by the Secretary of the Navy, Washington, DC (US)

(72) Inventor: Stephanie Kay Venn-Watson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/393,799

(22) Filed: Dec. 29, 2016

(65) Prior Publication Data
US 2018/0185316 A1 Jul. 5, 2018

(51) Int. Cl.
A61K 31/20 (2006.01)
A61K 45/06 (2006.01)

(52) U.S. Cl.
CPC .............. *A61K 31/20* (2013.01); *A61K 45/06* (2013.01)

(58) Field of Classification Search
CPC .................................................... A61K 31/20
See application file for complete search history.

(56) References Cited

U.S. PATENT DOCUMENTS

2016/0193170 A1   7/2016   Venn-Watson

FOREIGN PATENT DOCUMENTS

WO   PCT/IB2015/050484   7/2015

OTHER PUBLICATIONS

Wang et al (Obesity, 2011, 19, 2404-2410).*
Robinson et al (Lipds, 2013, 48:319-332).*
Calder (Am.J.Clin.Nutr, 2006;83(suppl):1505S-19S).*
Nanji et al (The Journal of Pharmacology and Experimental Therapeutics, 2001, vol. 299, No. 2, pp. 638-644).*
Targher G, Zenari L, Bertolini L, Muggeo M, Zoppini G (2001) Elevated levels of interleukin-6 in young adults with type 1 diabetes without clinical evidence of microvascular and macrovascular complcations. Diab Care 24956-957.
Colegrove K and Venn-Watson S (2015) Histomorphology of the bottlenose dolphin (*Tursiops truncatus*) pancreas and association of increasing islet β-cell size with chronic hypercholesterolemia. J Gen Camp Endocrinol 14:17-23.
Venn-Watson (2012) Hemochromatosis and fatty change: building evidence for insulin resistance in bottlenose dolphins (*Tursiops truncatus*). J Zoo Wildlf Med 43:S35-S47.
Venn-Watson S. (2007) Big brains and blood glucose: Common ground for diabetes mellitus in humans and healthy dolphins. Comp Med 57:390-5.
Venn-Watson S. (2013) Blood-Based Indicators of Insulin Resistance and Metabolic Syndrome in Bottlenose Dolphins (*Tursiops truncatus*). Front Endocrinol (Lausanne) 4:136.
Venn-Watson S. (2011) Dolphins as animal models for type 2 diabetes: Sustained, postprandial hyperglycemia and hyperinsulinemia. Gen Comp Endocrin 170:193-9.
Venn-Watson S. (2014) Dolphins and Diabetes: Applying One Health for breakthrough discoveries. Front Endocrinol DOI 10.3389/fendo.2014.00227.
Venn-Watson S. (2015) Increased dietary intake of saturated fatty acid heptadecanoic acid (C17:0) associated with decreasing ferritin and alleviated metabolic syndrome in dolphins. Plos One 10:e0132117.
Sobolesky PM, Harrell T, Parry C, Venn-Watson S, Janech MG (2016) Feeding a modified diet to bottlenose dolphins leads to an increase in serum adiponectin and sphingolipids consistent with improved insulin sensitivity. Front Endocrinol 7:33.
Venn-Watson S, Carlin K, Andrews GA, Chavey PS, Mazzaro L (2013) Associations of ceruloplasmin and haptoglobin with inflammation and glucose in bottlenose dolphins (*Tursiops truncatus*) J Comp Clin Path DOI: 10.1007/s00580-013-1738-0.
Venn-Watson S, Smith CR, Gomez F, Jensen ED (2011) Physiology of aging among healthy, older bottlenose dolphins (*Tursiops truncatus*): comparisons with aging humans. J Comp Phys B 181:667-680.
Zandman-Goddard G, Shoenfeld Y (2008) Hyperferritinemia in autoimmunity. IMAJ 10: 83-84.
Fave, G., Coste TC, Armand M (2004) Physiochemical properties of lipids: new strategies to manage fatty acid bioavailability. Cell Mol Biol 50:815-831.
Ramirez, M., Amante, L., Gil, A. (2001) Absorption and distribution of dietary fatty acids from different sources. Early Hum Develop 65:S95-S101.
Craik J (1998) GLUT-1 mediation of rapid glucose transport in dolphin (*Tursiops truncatus*) red blood cells. Am J Physiol 274:R112-R9.
McGowen M. (2012) Dolphin genome provides evidence for adaptive evolution of nervous system genes and a molecular rate slowdown. Royal Society Proc B 279:3643-51.
Jenkins B. (2015) A review of odd-chain fatty acid metabolism and the role of pentadecanoic acid (C15:0) and heptadecanoic acid (C17:0) in health and disease. Molecules 20:2425-44.
HL (2008) Fatty acids in bovine milk fat. Food Nutr Res 52:4;
Magnusdottir OK. (2014) Plasma alkylresorcinols C17:0/C21:0 ratio, a biomarker of relative whole-grain rye intake, is associated to insulin sensitivity: a randomized study.
Eur J Clin Nutr 68:453-458; Luzia LA. (2013) The influence of season on the lipid profiles of five commercially important species of Brazilian fish. Food Chem 83:93-97.
Benatar JR. (2014) The effects of changing dairy intake on trans and saturated fatty acid levels—results from a randomized controlled study. Nutr J 13:32. doi: 10.1186/1475-2891-13-32 PMID:24708591.

(Continued)

*Primary Examiner* — Sudhakar Katakam
(74) *Attorney, Agent, or Firm* — SPA WAR Systems Center Pacific; Kyle Eppele; Susanna J. Torke

(57) ABSTRACT

Compositions including an fatty acid, such as an odd chain fatty acid or a very long even chain fatty acid, and salts and derivatives thereof, and methods for treatment and prophylaxis of conditions related to inflammation and conditions related to inflammation, including anemia of chronic disease, insulin resistance, metabolic syndrome, autoimmune disease, hypertension, diabetes, nonalcoholic fatty liver disease, cardiovascular disease, cancer, aging, neurodegenerative diseases, including Alzheimer's disease and other forms of dementia, and other related conditions, and other related conditions.

12 Claims, 14 Drawing Sheets

(56) References Cited

OTHER PUBLICATIONS

Abdullah MM. (2015) Recommended dairy product intake modulates circulating fatty acid profile in healthy adults: a multi-centre cross-over study. Br J Nutr 113:435-44.

Forouhi N. (2014) Differences in the prospective association between individual plasma phospholipid saturated fatty acids and incident type 2 diabetes: the EPIC-InterAct case-cohort study. Lancet Diabetes Endocrinol 2:810-8.

Patel P. (2010) Fatty acids measured in plasma and erythrocyte-membrane phospholipids and derived by food-frequency questionnaire and the risk of new-onset type 2 diabetes: a pilot study in the European Prospective Investigation into Cancer and Nutrition (EPIC)-Norfolk cohort. Am J Clin Nutrition 92:1214-22.

Krachler B. (2008) Fatty acid profile of the erythrocyte membrane preceding development of Type 2 diabetes mellitus. Nutrition, metabolism, and cardiovascular diseases. NMCD 18:503-10.

Maruyama C. (2008) Differences in serum phospholipid fatty acid compositions and estimated desaturase activities between Japanese men with and without metabolic syndrome. J Atherscler Thromb 15:306-313.

Choi H. (2005) Dairy consumption and risk of type 2 diabetes mellitus in men: a prospective study. JAMA Internal Med 165:997-1003.

Kratz M. (2014) Dairy fat intake is associated with glucose tolerance, hepatic and systemic insulin sensitivity, and liver fat but not beta-cell function in humans. The American Journal of Clinical Nutrition. 99:1385-96.

Pereira M. (2002) Dairy consumption, obesity, and the insulin resistance syndrome in young adults: the CARDIA study. JAMA 287:2081-9.

Pfeuffer M and Schrezenmeir J (2006) Milk and the metabolic syndrome. Obesity Rev 8:109-18.

Ruidavets JB. (2007) High consumptions of grain, fish, dairy products and combinations of these are associated with a low prevalence of metabolic syndrome. J Epidemiol Community Health 61:810-817. PMID: 17699537.

Wells RS. (2013) Evaluation of potential protective factors against metabolic syndrome in bottlenose dolphins: feeding and activity patterns of dolphins in Sarasota Bay, Florida. Frontiers Endo 4:139.

Ellervik C. (2001) Prevalence of hereditary haemochromatosis in late-onset type 1 diabetes mellitus: a retrospective study. Lancet 358:1405-1409. PMID: 11705485.

Wells RS. (2004) Bottlenose dolphins as marine ecosystem sentinels: developing a health monitoring system. EcoHealth 1:246-254.

Barros NB. (1998) Prey and feeding patterns of resident bottlenose dolphins (*Tursiops truncatus*) in Sarasota Bay, Florida. J Mammal 79:1045-1059.

Berens-McCabe E. (2010) Prey selection by resident common bottlenose dolphin (*Tursiops truncatus*) in Sarasota Bay, Florida. Marine Biol 157:931-942.

Lagerstedt SA, Hinrichs DR, Batt SM, Magera MJ, Rinaldo P, McConnell JP (2001) Quantitative determination of C8-C26 total fatty acids for the biochemical diagnosis of nutritional and metabolic disorders. Mol Gen Metabol 73:38-45.

Anderson AJC (1954) Margarine. London. Pergamon Press; Mansson HL (2008) Fatty acids in bovine milk fat. Food Nutr Res 52:4.

Fernandes R. (2013) Relationship between acute phase proteins and serum fatty acid composition in morbidly obese patients. Dis Markers 35:104-102.

Forouhi NG. (2014) Differences in the prospective association between individual plasma phospholipid saturated fatty acids and incident type 2 diabetes: the EPIC-InterAct case-cohort study. Lancet Diabetes Endocrinol 2:810-818. doi: 10.1016/S2213-8587(14)70146-9 PMID: 25107467.

Slifka KA. (2013) Comparative diet analysis of fish species commonly consumed by managed and free-ranging bottlenose dolphins (*Tursiops truncatus*). Int J Vet Med 10:1.

Ozogul Y. (2007) Fatty acid profiles and fat contents of commercially important seawater and freshwater fish species of Turkey: A comparative study. Food Chem 103:217-223.

Venn-Watson S. (2015) Adrenal gland and lung lesions in Gulf of Mexico common bottlenose dolphins (*Tursiops runcatus*) found dead following the Deepwater Horizon oil spill. Plos One 10(5):e0126538. doi: 10.1371/journal.pone.0126538 PMID: 25992681.

Venn-Watson S. (2015) Annual survival, mortality, and longevity of bottlenose dolphins (*Tursiops truncatus*) at the U.S. Navy Marine Mammal Program, 2004-2013. J Am Vet Med 246:893-898.

Venn-Watson S. (2008) Clinical relevance of elevated transaminases in a bottlenose dolphin (*Tursiops truncatus*) population. J Wildlf Dis 44:318-330.

Akbar, H. (2015). Alterations in Hepatic FGF21, Co-Regulated Genes, and Upstream Metabolic Genes in Response to Nutrition, Ketosis and Inflammation in Peripartal Holstein Cows. PLoS One 10, e0139963. doi: 10.1371/journal.pone.0139963.

Annual, seasonal and individual variation in hematology and clinical blood chemistry profiles in bottlenose dolphins (*Tursiops truncatus*) from Sarasota Bay, Florida. Comp Biochem Physiol A Mol Integr Physiol 148, 266-277. doi: 10.1016/j.cbpa.2007.04.017.

Bartke, N. and Hannun, Y.A. (2009) Bioactive sphingolipids: metabolism and function. J Lipid Res S91-S96.

Hassanali, Z., et al. (2010). Dietary supplementation of n-3 PUFA reduces weight gain and improves postprandial lipaemia and the associated inflammatory response in the obese JCR:LA-cp rat. Diabetes Obes Metab 12, 139-147. doi: 10.1111/j.1463-1326.2009.01130.x.

Profenno LA, Porsteinsson AP, Faraone SV (2010) Meta-analysis of Alzheimer's disease risk with obesity, diabetes, and related disorders. Biol Psych 67:505-512.

Di Paolo G, Kim TW (2011) Linking lipids to Alzheimer's disease: cholesterol and beyond. Nature Rev Neurosci 12.

Stephenson D, Perry D, Carillo MC, Sperling R, Katz R, Berry D et al. (2015) Building a roadmap for developing combination therapies for Alzheimer's disease. Expert Rev Neurother 15:327-333.

Heneka MT, Carson MJ, Khoury JE, Landreth GE, Brosseron F, Feinstein DL, et al. (2015) Neuroinflammation in Alzheimer's disease. Lancet Neural 14:388-405.

Ahmad R, Al-Mass A, Al-Ghawas D, Shareif N, Zghoul N, Melhem M, Hasan A, Al-Ghimlas F, Dermime S, Behbehani K (2013) Interaction of osteopontin with IL-18 in obese individuals: implications for insulin resistance. PLOS ONE 8: e63944.

Bettcher BM, Fitch R, Wynn MJ, Lalli MA, Elofson J, Jastrzab L, et al. (2016) MCP-1 and eotaxin-1 selectively and negatively associate with memory in MCI and Alzheimer's disease dementia phenotypes. Alz Dement: Diag Assess Dis Monit 3:91-97.

Bossu P, Ciaramella A, Salani F, Bizzoni F, Varsi E, Iolio FD et al. (2008) Interleukin-18 produced by peripheral blood cells is increased in Alzheimer's disease and correlates with cognitive impairment. Brain, Behav, Immun 22:487-492.

Dursun E, Gezen-Ak D, Hanagasi H, Bilgic B, Lohmann E, Ertan S, et al. (2015) The interleukin 1 alpha, interleukin 1 beta, interleukin 6 and alpha-2-macroglobin serum levels in patients with early or late onset Alzheimer's disease, mild cognitive impairment or Parkinson's disease. J Neuroinflamm 283: 50-57.

Holmes C, Cunningham C, Zotova E, Woolford J, Dean C, Kerr S, Culliford D, Perry VH (2009) Systemic inflammation and disease progression in Alzheimer disease. Neurology 73:768-774.

Kanda H, Tateya S, Tamori Y, Kotani K, Hiasa KI, Kitazawa R, Kitazawa S, Miyahi H, Maeda S, Egashira K, Kasuga M (2006) MCP-1 contributes to macrophage infiltration into adipose tissue, insuin resistance, and hepatic steatosis in obesity. J Clin Invest 116:1494-1505.

T. Kiyota, M. Yamamoto, H. Xiong, M.P. Lambert, W.L. Klein, H.E. Gendelman, et al. CCL2 accelerates microglia-mediated Abeta oligomer formation and progression of neurocognitive dysfunction PLoS One, 4 (2009), p. e6197.

Martin-Jimenez CA, Gaitan-Vaca DM, Echeverria V, Gonzalez J (2016) Relationship between obesity, Alzheimer's disease, an Parkinson's disease: an astrocentric view. Mol Neurobiol. DOI: 10.1007/s12035-016-0193-8.

(56) References Cited

OTHER PUBLICATIONS

Ojala J, Alafuzoff I, Herukka SK, van Groen T, Tanila H, Pierttila T (2009) Expression of interleukin-18 is increased in the brains of Alzheimer's disease patients. Neurobiol Aging 30:198-209.

Panee J (2012) Monocyte chemoattractant protein 1 (MCP-1) in obesity and diabetes. Cytokine 60:1-12.

Perry, V.H., Teeling, J. (2013) Microglia and macrophages of the central nervous system: the contribution of microglia priming and systemic inflammation to chronic neurodegeneration. Semin Immunopathol 35:601-612.

J. Ross, S. Sharma, J. Winston, M. Nunez, G. Bottini, M. Franceschi, et al. CHF5074 reduces biomarkers of neuroinflammation in patients with mild cognitive impairment: a 12-week, double-blind, placebo-controlled study Curr Alzheimer Res, 10 (2013), pp. 742-753.

Salameh TS, Rhea EM, Banks WA, Hanson AJ (2016) Insulin resistance, dyslipidemia, and apolipoprotein E interactions as mechanisms in cognitive impairment and Alzheimer's disease. Exp Biol Med doi: 10.1177/1535370216660770.

Sindhu S, Thomas R, Shihab P, Sriraman D, Behbehani K, Ahmad R (2015) Obesity is a positive modulator of IL-6R and IL-6 expression in subcutaneous adipose tissue: significance for metabolic inflammation. Plos One.

Tucsek Z, Toth P, Sosnowska D, Gautam T, Mitschelen M, Koller A, Szalai G, Sonntag WE, Ungvari Z, Csiszar A (2013) Obesity in aging exacerbates blood-brain barrier disruption, neuroinflammation, and oxidative stress in the mouse hippocampus: effects on expression of genes involved in beta-amyloid generation and Alzheimer's disease. 69:1212-1226.

Van Eldik LJ, Carrillo MC, Cole PE, Feuerbach D, Greenberg BD, Hendrix JA, et al. (2016) The roles of inflammation and immune mechanisms in Alzheimer's disease. Alz Demen: Transl Res Clin Intery 2:99-109.

Wu YY, Hsu JL, Wang HC, Wu SJ, Hong CJ, Cheng IHJ (2015) Alterations of the neuroinflammatory markers IL-6 and TRAIL in Alzheimer's disease. Dement Geriat Cogn Disord Extra 5:424-434.

\* cited by examiner

COMPOSITIONS AND METHODS FOR DIAGNOSIS AND TREATMENT OF INFLAMMATION

STATEMENT REGARDING FEDERALLY SPONSORED R&D

The United States Government has ownership rights in this invention, pursuant to passing of title to a Subject Invention under Federal Grant N00014-15-1-2131 (National Marine Mammal Foundation). Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil, referencing NC 105245.

FIELD OF THE INVENTION

Compositions including fatty acids, such as an odd chain saturated fatty acid or a very long even chain saturated fatty acid, and salts and derivatives thereof, and methods for treatment or prophylaxis of inflammation and conditions related to inflammation, including cardiometabolic diseases, cancer, and conditions of aging, are provided, including compositions and methods for treating inflammation and conditions related to inflammation, including anemia of chronic disease, autoimmune disease, nonalcoholic fatty liver disease, cardiovascular disease, cancer, aging, neurodegenerative diseases, including Alzheimer's disease and other forms of dementia, and other related conditions.

BACKGROUND OF THE INVENTION

Inflammation is indicated by detection of erythrocyte sedimentation rate, C-reactive protein, cytokines and other markers in the blood being high, and/or alkaline phosphatase in the blood being low for a sustained period of time. Chronic inflammation may occur from untreated causes of acute inflammation or may develop over months without a known acute cause. Chronic inflammation is a common component of highly prevalent diseases, including obesity, diabetes, metabolic syndrome, cancer, cardiovascular diseases and diseases of aging. Inflammation has been identified as a causative or contributing factor to these conditions, and as such, inflammation has been proposed as a therapeutic target to prevent, manage, and treat these conditions.

SUMMARY OF THE INVENTION

Compositions and methods for treatment or prophylaxis of inflammation and associated conditions are provided. These compositions comprise one or more fatty acids, derivatives of fatty acids, or salts thereof, which may be administered in combination with other medicaments or as part of various treatment regimens as described herein. The provided compositions are effective for modulating markers associated with chronic inflammation. Methods are provided for administering the compositions.

Accordingly, in a generally applicable first aspect (i.e., independently combinable with any of the aspects or embodiments identified herein), a pharmaceutical composition is provided comprising: one or more fatty acids, or pharmaceutically acceptable salts thereof, wherein the one or more fatty acids are selected from the group consisting of odd chain fatty acids and very long even chain fatty acids; and a pharmaceutically acceptable carrier.

In an embodiment of the first aspect (i.e., independently combinable with any of the aspects or embodiments identified herein), the one or more fatty acids is heptadecanoic acid or pentadecanoic acid.

In an embodiment of the first aspect (i.e., independently combinable with any of the aspects or embodiments identified herein), the composition is substantially free from even chain fatty acids.

In an embodiment of the first aspect (i.e., independently combinable with any of the aspects or embodiments identified herein), the one or more fatty acids is behenic acid or lignoceric acid.

In an embodiment of the first aspect (i.e., independently combinable with any of the aspects or embodiments identified herein), the composition comprises at least one odd chain fatty acid and at least one very long even chain fatty acid.

In an embodiment of the first aspect (i.e., independently combinable with any of the aspects or embodiments identified herein), the one or more fatty acids comprises heptadecanoic acid and behenic acid.

In an embodiment of the first aspect (i.e., independently combinable with any of the aspects or embodiments identified herein), the composition is in a unit dosage form.

In an embodiment of the first aspect (i.e., independently combinable with any of the aspects or embodiments identified herein), the pharmaceutical composition is configured for administration of from 2.5 mg to 11 mg, per 1 kg of body weight, of the one or more fatty acids or pharmaceutically acceptable salts thereof to a patient.

In an embodiment of the first aspect (i.e., independently combinable with any of the aspects or embodiments identified herein), the pharmaceutical composition is configured for administration once per day.

In an embodiment of the first aspect (i.e., independently combinable with any of the aspects or embodiments identified herein), the pharmaceutical composition comprises from 0.01 mg to 10000 mg of the one or more fatty acids or pharmaceutically acceptable salts thereof.

In a generally applicable second aspect (i.e., independently combinable with any of the aspects or embodiments identified herein), use is provided of a pharmaceutical composition of the first aspect or any embodiment thereof, in the manufacture of a medicament for treatment or prophylaxis of inflammation and conditions related to inflammation, wherein the conditions related to inflammation are selected from the group consisting of anemia of chronic disease, insulin resistance, metabolic syndrome, autoimmune disease, hypertension, diabetes, nonalcoholic fatty liver disease, cardiovascular disease, cancer, aging, neurodegenerative diseases, Alzheimer's disease, and dementia.

In an embodiment of the second aspect (i.e., independently combinable with any of the aspects or embodiments identified herein), the use is in the manufacture of a medicament for treatment or prophylaxis of inflammation.

In an embodiment of the second aspect (i.e., independently combinable with any of the aspects or embodiments identified herein), the pharmaceutical composition is configured to modulate a marker of inflammation or a symptom of inflammation.

In an embodiment of the second aspect (i.e., independently combinable with any of the aspects or embodiments identified herein), the marker of inflammation is selected from the group consisting of odd chain fatty acid percentage, serum concentration of an odd chain fatty acid, red blood cell membrane concentration of an odd chain fatty acid, serum total odd chain fatty acids, red blood cell membrane total odd chain fatty acids, serum ferritin, erythrocyte sedimentation rate, serum alkaline phosphatase, serum CRP, IL-6, TNFα, c-Jun N-terminal kinase, ATM and monocyte-chemoattractant protein-1.

In an embodiment of the second aspect (i.e., independently combinable with any of the aspects or embodiments identified herein), the pharmaceutical composition is configured to increase a serum concentration or a red blood cell membrane concentration of the one or more fatty acids by at least about $0.001 \times 10^{-4}$ M above a pretreatment value.

In a generally applicable third aspect (i.e., independently combinable with any of the aspects or embodiments identified herein), a method of treatment or prophylaxis of inflammation and conditions related to inflammation, including anemia of chronic disease, insulin resistance, metabolic syndrome, autoimmune disease, hypertension, diabetes, nonalcoholic fatty liver disease, cardiovascular disease, cancer, aging, neurodegenerative diseases, including Alzheimer's disease and other forms of dementia, and other related conditions, comprising: administering to a patient in need thereof, an effective amount of one or more fatty acids, or pharmaceutically acceptable salts thereof, wherein the one or more fatty acids are selected from the group consisting of one or more odd chain fatty acids, one or more very long even chain fatty acids, and combinations thereof.

In an embodiment of the third aspect (i.e., independently combinable with any of the aspects or embodiments identified herein), the one or more fatty acids or pharmaceutically acceptable salts thereof is provided as a pharmaceutical composition in a unit dosage form comprising the one or more fatty acids or pharmaceutically acceptable salts thereof and a pharmaceutically acceptable carrier.

In an embodiment of the third aspect (i.e., independently combinable with any of the aspects or embodiments identified herein), the unit dosage form comprises from 0.01 mg to 10000 mg of the one or more fatty acids or pharmaceutically acceptable salts thereof.

In an embodiment of the third aspect (i.e., independently combinable with any of the aspects or embodiments identified herein), the one or more odd chain fatty acids is heptadecanoic acid or pentadecanoic acid.

In an embodiment of the third aspect (i.e., independently combinable with any of the aspects or embodiments identified herein), the pharmaceutical composition is substantially free from even chain fatty acids.

In an embodiment of the third aspect (i.e., independently combinable with any of the aspects or embodiments identified herein), the one or more very long even chain fatty acids is behenic acid or lignoceric acid.

In an embodiment of the third aspect (i.e., independently combinable with any of the aspects or embodiments identified herein), the pharmaceutical composition comprises a plurality of different fatty acids.

In an embodiment of the third aspect (i.e., independently combinable with any of the aspects or embodiments identified herein), from 2.5 mg to 11 mg of the one or more fatty acids or pharmaceutically acceptable salts thereof is administered to the patient, per 1 kg of body weight, per day.

In an embodiment of the third aspect (i.e., independently combinable with any of the aspects or embodiments identified herein), the one or more fatty acids or pharmaceutically acceptable salts thereof is administered to the patient once per day.

In an embodiment of the third aspect (i.e., independently combinable with any of the aspects or embodiments identified herein), a serum concentration or a red blood cell membrane concentration of the one or more fatty acids is increased by at least about $0.001 \times 10^{-4}$ M above a pretreatment value.

In a generally applicable fourth aspect (i.e., independently combinable with any of the aspects or embodiments identified herein), a composition substantially as described herein is provided.

In a generally applicable fifth aspect (i.e., independently combinable with any of the aspects or embodiments identified herein), a composition substantially as described herein is provided.

In a generally applicable sixth aspect (i.e., independently combinable with any of the aspects or embodiments identified herein), a use substantially as described herein is provided.

DETAILED DESCRIPTION

Figure 1A:
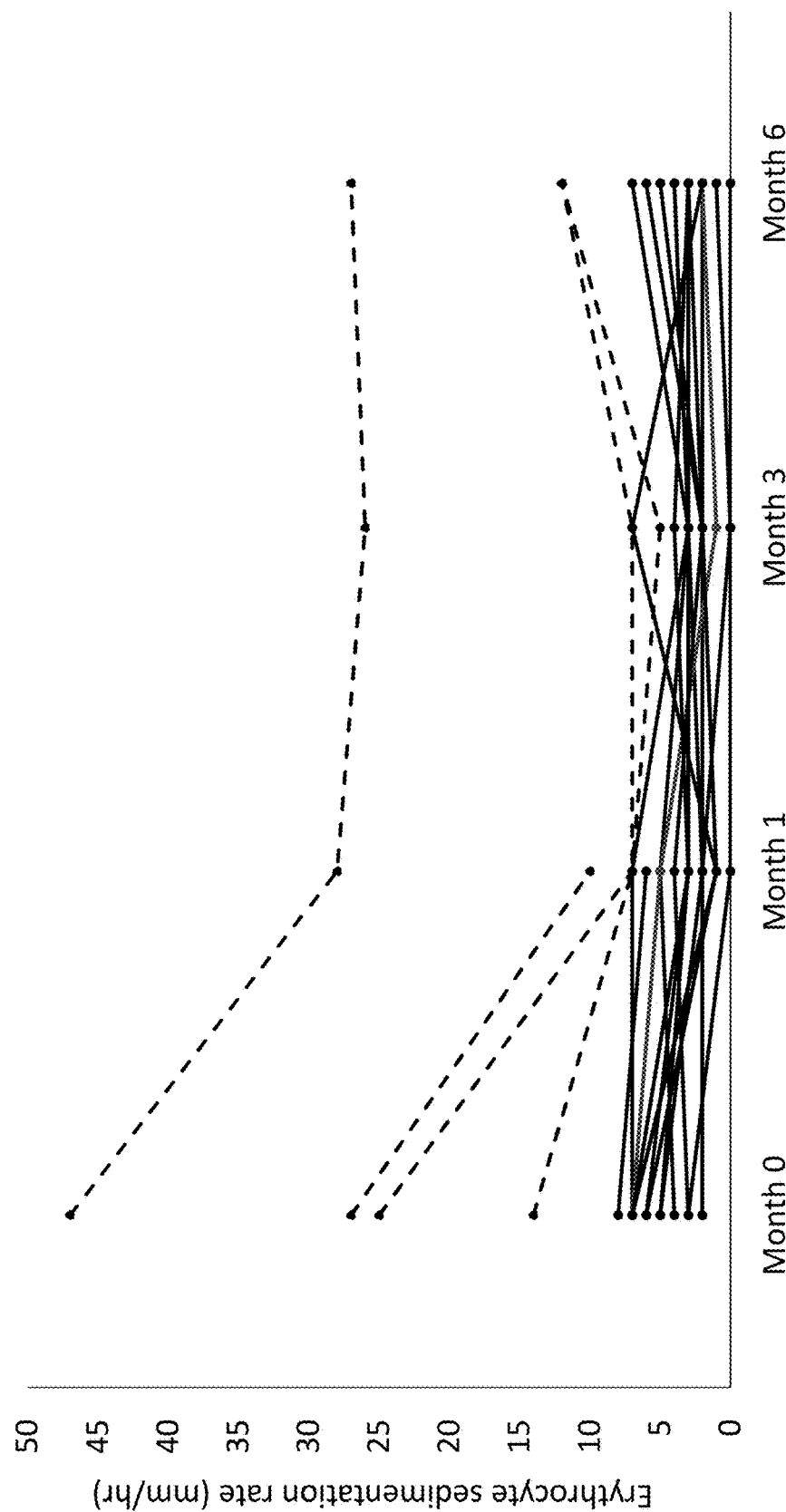
FIGS. 1A-1B provide data on lowered erythrocyte sedimentation rate and alkaline phosphatase among individual dolphins while on the modified fish diet. The dotted line on FIG. 1A represents study animals in which inflammation (or high erythrocyte sedimentation rate) decreased while on modified diet. The dotted line on FIG. 1B represents study animals in which inflammation (high alkaline phosphatase) decreased while on a modified diet.

Compositions including one or more fatty acids, and associated methods for treatment of conditions related to inflammation and associated conditions, including anemia of chronic disease, insulin resistance, metabolic syndrome, autoimmune disease, hypertension, diabetes, nonalcoholic fatty liver disease, cardiovascular disease, cancer, aging, neurodegenerative diseases, including Alzheimer's disease and other forms of dementia, and other related conditions, are provided.

Chronic inflammation is a subclinical condition involving raised and prolonged activation of the immune system, including raised pro-inflammatory cytokine levels. Cytokines, including tumor necrosis factor alpha (TNF-α), interleukin 6 (IL-6), interleukin 1 beta (IL-β), interleukin 18 (IL-18), and monocyte chemoattractant protein-1 (MCP-1), as well as other components of chronic inflammation, have been identified as underlying causes of or contributors to cardiovascular disease, including atherosclerosis. Systemic inflammation results in endothelial cell dysfunction, changes in vascular tone, and up-regulation of coagulation, which in turn cause atherosclerosis and broad cardiovascular disease complications.

Chronic inflammation has been recognized as an underlying driver of metabolic syndrome, a broad spectrum disorder of energy utilization and storage. Cytokines, including IL-6, IL-1β, IL-18, and MCP-1, as well as other components of chronic inflammation, have been identified as underlying causes of or contributors to metabolic syndrome. Metabolic syndrome affects an estimated one in four people globally and one in three people, in the United States. It is associated with the risk of developing cardiovascular disease, diabetes (especially type 2 diabetes), and other conditions such as polycystic ovary syndrome, fatty liver disease, nonalcoholic steatohepatitis, cholesterol gallstones, asthma, sleep disturbances, and some forms of cancer. Metabolic syndrome is characterized by abdominal (central) obesity, elevated blood pressure, elevated insulin, elevated fasting plasma glucose, elevated serum triglycerides, decreased high-density lipoprotein (HDL) levels, proinflammatory state (recognized clinically by elevations of C-reactive protein (CRP)), and a prothrombotic state.

Anemia of chronic disease, also called anemia of inflammation and inflammatory anemia, is anemia associated with a chronic underlying condition. The underlying condition, which may be, for example, infections, inflammation, or cancer, may reduce oxygen-carrying capacity by a number of mechanisms, generally related to reducing the population of circulating RBCS. Generally, ACD develops and presents slowly, with mild or no symptoms.

Inflammation has been recognized as an important underlying driver of cancer, serving as both a nidus for tumor proliferation and orchestrator of tumor cell survival and migration. As such, anti-inflammatory agents have been proposed as promising therapeutic options for cancer patients.

Inflammation is a key component of autoimmune diseases, including systemic lupus erythematous, rheumatoid arthritis, multiple myeloma, multiple sclerosis, and psoriasis. IL-6 is known to or may play an important role in the pathogenesis of many autoimmune diseases, including but not limited to type 1 diabetes and rheumatoid arthritis, and as such, anti-IL-6 molecules are candidate therapeutics for autoimmune disease.

Aging refers to a series of morphological and functional changes in an organism which take place over time. The term also refers to the deterioration of the biological functions after an organism has attained its maximum reproductive potential. It is thought that inflammation may be related to aging through mutation to mitochondrial DNA and other processes. Cytokines, including IL-6, IL-18, and MCP-1, as well as other components of inflammation, have been identified as underlying causes of or contributors to aging-associated complications. Reducing inflammation may slow the degenerative process of aging.

Subjects suffering from a neurodegenerative condition, such as, for example, Alzheimer's disease, may display inflammation long before dementia is detected clinically. Amyloid beta, a peptide thought to be implicated in the development of neurodegenerative disease, may be correlated to inflammation and associated raised cytokines, which may in turn lead to neuron damage. Cytokines, including IL-6, IL-18, and MCP-1, as well as other components of inflammation, have been identified as underlying causes of or contributors to dementia, including Alzheimer's disease. Reducing inflammation may also protect neurons against amyloid beta toxicity, reduce the risk of developing, or prevent the progression of dementia, including Alzheimer's disease.

It is an object of certain of the embodiments to provide a method for detecting protective factors for and risk factors against conditions provided herein, including but not limited to inflammation and associated conditions such as cardiovascular disease, insulin resistance, metabolic syndrome, autoimmune disease, hypertension, diabetes, anemia of chronic disease, nonalcoholic fatty liver disease, cancer, aging, neurodegenerative diseases, including Alzheimer's disease and other forms of dementia, and other related conditions in mammal subjects, such as dolphins and humans. An object of certain of the embodiments is to provide a method for treating conditions including but not limited to inflammation in mammal subjects, such as dolphins and humans. An object of certain of the embodiments is to provide a method for detecting conditions including but not limited to inflammation in mammal subjects, such as for dolphins and humans. It is an object of certain of the embodiments to provide a method for increasing the serum, plasma, or erythrocyte membrane level of one or more fatty acids or fatty acid derivatives, including but not limited to odd chain fatty acids, for example, heptadecanoic acid, and/or certain even chain fatty acids, such as behenic acid, in mammal subjects, such as dolphins and humans. An object of certain of the embodiments is to provide a fatty acid supplement or prescription therapeutic for treating or preventing a condition including but not limited to inflammation. An object of certain of the embodiments is to provide a method for detecting and/or treating a condition provided herein including inflammation in mammal subjects, such as dolphins and humans, that is easy to accomplish in a cost-effective manner.

An object of certain of the embodiments is to provide a method for modulating markers of inflammation in mammal subjects, such as dolphins and humans. An object of certain of the embodiments is to provide a method for detecting inflammation in mammal subjects, such as dolphins and humans. An object of certain of the embodiments is to provide a method for treatment of inflammation in mammal subjects, such as dolphins and humans. An object of certain of the embodiments is to provide a method for prophylaxis of inflammation in mammal subjects, such as dolphins and humans. An object of certain of the embodiments is to provide a method for prophylaxis of a condition provided herein including inflammation and associated conditions, including anemia of chronic disease, insulin resistance, metabolic syndrome, autoimmune disease, hypertension, diabetes, nonalcoholic fatty liver disease, diseases of aging, cardiovascular disease, cancer, neurodegenerative diseases, including Alzheimer's disease and other forms of dementia, in mammal subjects, such as dolphins and humans.

An object of certain of the embodiments is to provide a method for increasing an odd chain fatty acid in the sera, plasma, or erythrocyte membranes of mammal subjects, such as dolphins and humans. An object of certain of the embodiments is to provide a method for increasing very long even chain fatty acids in the sera of mammal subjects, such as dolphins and humans. An object of certain of the embodiments is to provide a method for detecting or treating inflammation in mammal subjects, such as dolphins and humans. An object of certain of the embodiments is to provide an odd chain fatty acid substantially free from other fatty acids in mammal subjects, such as dolphins and humans. An object of certain of the embodiments is to provide one or more odd chain fatty acids substantially free from even chain fatty acids in mammal subjects, such as dolphins and humans.

It is an object of certain of the embodiments is to provide a method for detecting and treating chronic inflammation in mammal subjects, such as dolphins and humans. An object of certain of the embodiments is to provide a fatty acid, such as an odd chain fatty acid or a very long even chain fatty acid, for treating chronic inflammation in mammal subjects, such as dolphins and humans. An object of certain of the embodiments is to provide a method for prophylaxis of inflammation in mammal subjects, such as dolphins and humans. An object of certain of the embodiments is to provide a method for detecting or treating a condition associated with inflammation in mammal subjects, such as dolphins and humans. An object of certain of the embodiments is to provide a behenic acid or other very long even chain saturated fatty acid supplement for treating inflammation in mammal subjects, such as dolphins and humans.

An object of certain of the embodiments is to provide a bioavailable form of odd chain and very long even chain fatty acids to mammal subjects, such as dolphins and humans. An object of certain of the embodiments is to provide one or more odd chain fatty acids with one or more certain even chain fatty acids to mammal subjects, such as dolphins and humans. An object of certain embodiments is to provide a method for increasing both an odd chain fatty acid and certain even chain fatty acids in the sera of mammal subjects, such as dolphins and humans. An object of certain of the embodiments is to provide a method for fatty acid elongation in the sera, plasma, or erythrocyte membranes of mammal subjects, such as dolphins and humans. An object of certain of the embodiments is to provide a method for fatty acid chain shortening in the sera, plasma, or erythrocyte membranes of mammal subjects, such as dolphins and humans. An object of certain of the embodiments is to provide a method for altering concentrations of a variety of odd chain and very long even chain fatty acid forms, including neutral forms (e.g. free fatty acids, cholesterol esters, diacylglycerides, and triacylglycerides), phospholipids (e.g. phosphatidylcholine, phosphatidylethanolamine, lysophosphatidylcholine, and lysophosphatidylethanolamine), and sphingolipids (e.g. ceramides, hexosylceramides, and sphingosines) in the sera, plasma, or erythrocyte membranes of mammal subjects, such as dolphins and humans.

Compositions including one or more of certain even chain fatty acids, and associated methods for treatment of inflammation are provided. Compositions including one or more bioavailable even chain fatty acids are provided.

One or more than one of the aforementioned objects is provided by or achieved by the various compositions, methods, and uses as described herein.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, phosphates, triphosphates, and β-sulfenyl derivatives.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, fatty acids, fatty alcohols, sterol and sterol derivatives, phospholipids, ceramides, sphingolipids, tocopherols, and carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

As used herein, a "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

As used herein, a "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

As used herein, a "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Any percentages, ratios or other quantities referred to herein are on a weight basis, unless otherwise indicated.

Odd Chain Fatty Acids and Very Long Even Chain Fatty Acids

Fatty acids include saturated and unsaturated fatty acids as provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation in a form total # carbons: # double bonds, $\Delta_{double\ bond\ positions}$ can be employed. For example, $20:4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta 9$-octadecenoate) is a monounsaturated fatty acid, linolenate (all-cis-$\Delta 9,12,15$-octadecatrienoate) is a polyunsaturated fatty acid. The total number of carbons can be preceded by "C" and double bond positions can be unspecified, e.g., C20:4 referring to a fatty acid having 20 carbon atoms and four double bonds.

A fatty acid may be referred to by various names, for example, heptadecanoic acid may be referred to as heptadecylic acid, margaric acid, and n-heptadecylic acid, or C17:0. A fatty acid may be referred to by lipid numbers, as known in the art.

In some embodiments, the fatty acid can be an odd chain fatty acid or a very long even chain fatty acid. In further embodiments, one or more fatty acids can include at least one odd chain fatty acid or at least one very long even chain fatty acid.

Examples of odd chain fatty acids are margaric acid (heptadecanoic acid, C17:0), pelargonate (nonanoic acid, C9:0), undecanoic acid (C11:0), nonadecanoic acid (C19:0), pentadecanoic acid (C15:0), arachidonate ((5Z,8Z,11Z, 14Z)-icosa-5,8,11,14-tetraenoic acid), adrenate (all-cis-7,10, 13,16-docosatetraenoic acid), and osbond acid (all-cis-4,7, 10,13,16-docosapentaenoic acid). Generally, the one or more odd chain fatty acids have from 9 carbon atoms to 31 carbon atoms (9, 11, 13, 15, 17, 19, 21, 23, 25, 27, 29, or 31 carbon atoms), for example, from 15 to 21 carbon atoms, for example 17 carbon atoms; however, in certain embodiments higher or lower odd numbers of carbon atoms can be acceptable. Generally, the one or more odd chain fatty acids are saturated; however, in certain embodiments mono or polyunsaturated odd chain fatty acids can be acceptable.

An odd chain fatty acid may include saturated or unsaturated hydrocarbon chains. An odd chain fatty acid may be present as a carboxylic derivative. An odd chain fatty acid may be present as a salt, for example, at the carboxylic group. In some embodiments, one odd chain fatty acid may be present, two odd chain fatty acids may be present, three odd chain fatty acids may be present, or more. In some embodiments, odd chain fatty acids in a mixture including a plurality of odd chain fatty acids may be distinguished by the amount of unsaturation, the length of the hydrocarbon chain, varying states of derivativeification, or by other structural features.

Odd chain fatty acids are found in trace amounts in some dairy products, including butter, and is a component of some fish (see, e.g., Mansson H L (2008), Fatty acids in bovine milk fat, Food Nutr. Res. 52:4, Luzia L A, Sampaio G R, Castellucci C M N, Torres E A F S (2013) The influence of season on the lipid profiles of five commercially important species of Brazilian fish. Food Chem. 83:93-97). Studies have demonstrated that increasing daily dietary intake of foods with odd chain fatty acids successfully increases serum or plasma levels (see, e.g., Benatar J. R., Stewart R. A. H. (2014), The effects of changing dairy intake on trans and saturated fatty acid levels—results from a randomized controlled study. Nutr. J. 13:32).

As used herein, the term "very long" as applied to fatty acids, such as even chain fatty acids, refers to those fatty acids having at least 20 carbon atoms, e.g., fatty acids having from 20 to 26 carbon atoms, for example, behenic acid (C22:0).

The one or more very long even chain fatty acids can have, for example, 20, 22, 24, 26, 28, or 30 carbon atoms; however, in certain embodiments higher or lower even numbers of carbon atoms can be acceptable. Generally, the one or more very long even chain fatty acids are saturated; however, in certain embodiments mono or polyunsaturated very long even chain fatty acids can be acceptable. A very long even chain fatty acid may be present as a carboxylic derivative. A very long even chain fatty acid may be present as a salt, for example, at the carboxylic group. In some embodiments, one very long even chain fatty acid may be present, two very long even chain fatty acids may be present, three very long even chain fatty acids may be present, or more.

In some embodiments, very long even chain fatty acids in a mixture including a plurality of very long even chain fatty acids may be distinguished by the amount of unsaturation, the length of the hydrocarbon chain, varying states of derivativeification, or by other structural features. The very long even chain fatty acid may be provided in a bioavailable form.

Very long even chain fatty acids are found in trace amounts in pracaxi oil, derived from the seeds of the *Pentaclethra macroloba* tree, and ben oil, derived from the seeds of *Moringa oleifera*. A pure or purified very long even chain fatty acid may exist in various physical states. For example, behenic acid exists as a white to cream color powder or crystals that is stable at room temperature. Behenic acid can be purchased in forms suitable for research purposes in small amounts from some commercial suppliers (for example, from Sigma-Aldrich corp., of St. Louis, Mo.). Other very long even chain fatty acids, or salts or derivatives thereof, may exist as oils, solids, crystalline solids.

Generally, a fatty acid, such as an odd chain fatty acid or a very long even chain fatty acid can be provided as a free fatty acid, or a derivative thereof. Such derivatives include, but are not limited to, acyl glycerides. An acyl glyceride may be substituted with up to three acyl fatty acid esters. Thus, an acyl glyceride can be a monoacylglyceride (MAG), diacylglyceride (DAG), or a triacylglyceride (TAG). The glyceride can include more than one type of fatty acid ester. For example, a glyceride can include a heptdecanoate and a docosanoate. A glyceride can also be a structured triacylglyceride (STAG), a plasmalogen, or a phospholipid. The fatty acid ester can be in the sn1 position or the sn2 position, or both positions. The sn1 and sn2 positions can be substituted by the same or different fatty acid esters. As a non-limiting example, a structured triacylglyceride can be sn-1, 3-C17-sn-2-oleoyl.

In some embodiments, a fatty acid can be provided as a free fatty acid, a cholesterol ester, a glycerol ester (including, but not limited to a monoacylglyceride (MAG), diacylglyceride (DAG), or a triacylglyceride (TAG)), a phospholipid (including, but not limited to, a phosphatidylcholine, a lysophosphatidylcholine, a phosphatidylethanolamine, a lysophosphatidylethanolamine, or a phosphatidylserine), a ceramide (including but not limited to a hexosyl ceramide) or a sphingolipid. A non-limiting example of a phophatidylcholine is 2,3-di-C17:0-phosphatidylcholine. A non-limiting example of a lysophophatidylcholine is 2-lyso-3-C17:0-phosphatidylcholine. In some embodiments, a derivative of a fatty acid can be a β-sulfenyl derivative. It is thought that β-sulfenyl derivative, such as an acid or ester, can be resistant to β-oxidation in the body. As a non-limiting example, the β-sulfenyl derivative of heptadecanoic acid is tetradecylthioacetic acid. Derivatives can be synthesized by standard methods known to those of skill in the art.

In some embodiments, a fatty acid may be provided as a constituent of a specific type of lipid, for example, a ceramide, a phospholipid, a sphingolipid, a membrane lipid, a glycolipid, or a triglyceride.

In some embodiments, a fatty acid, such as a very long even chain fatty acid, is provided in a bioavailable form. The term "bioavailability" refers to the fraction of an administered dose of unchanged drug that reaches the systemic circulation, one of the principal pharmacokinetic properties of drugs. By definition, when a medication is administered intravenously, its bioavailability is 100%. As employed herein, the term "bioavailable" refers to a form of the fatty acid that is successfully absorbed by the body when using methods of adminstration other than intravenous, for example, an oral therapeutic). In some embodiments, very long even chain fatty acid-based compositions may include adaptions that optimize absorption. In some embodiments, a very long even chain fatty acid can be provided as a structured triacylglyceride. In further embodiments, the fatty acid is in the sn-2 position of a structured triacylglyceride.

A pure or purified fatty acid may exist in various physical states. For example, heptadecanoic acid exists as an off-white powder that is stable at room temperature; this compound can be purchased in forms suitable for research purposes in small amounts from some commercial suppliers (for example, from Sigma-Aldrich corp., of St. Louis, Mo.). Other fatty acids, or salts or derivatives thereof, may exist as oils, solids, crystalline solids, or gases.

An odd chain fatty acid or a very long even chain fatty acid, or the pharmaceutically acceptable salts or derivatives thereof, may be provided in a purity (e.g., a percentage of the fatty acid, or its pharmaceutically acceptable salts or derivatives, in a bulk form) of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, wherein substantially pure may include, but not be limited to, a product with impurities at a level such that no physiological effect from the presence of the impurities is detectable. A mixture of fatty acids, such as, for example, odd chain fatty acids and/or very long even chain fatty acids, or pharmaceutically acceptable salts or derivatives thereof, may be present in a purity of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure. The fatty acid, or a mixture thereof, or a pharmaceutically acceptable salt or derivative thereof, may be free from other fatty acids or fatty acid derivatives, may be free from triglycerides, or may be free from phospholipids. Without limitation, an odd chain fatty acid as provided herein may be substantially free from even chain fatty acids, singly or taken as a group; even chain fatty acids include, for example, myristic acid (C14:0), palmitic acid (C16:0), or stearic acid (C18:0). In some embodiments, an odd chain fatty acid as provided herein may be substantially free from short-chain fatty acids (SCFA), medium-chain fatty acids (MCFA), long-chain fatty acids (LCFA), or very long chain fatty acids (VLCFA).

A fatty acid, such as an odd chain fatty acid or a very long even chain fatty acid, or a pharmaceutically acceptable salt or derivative thereof, may be from any source. In some embodiments, a fatty acid, or its pharmaceutically acceptable salts or derivatives, may be present in natural sources, may be isolated from natural sources, may be semi-synthetic, may be synthetic, or may be a mixture of one or more of these. The fatty acid, or its pharmaceutically acceptable salts or derivatives, may be produced in a laboratory, may be produced in nature, may be produced by enzymatic processes, may be produced by wild microbes, may be produced by genetically modified microbes, may be isolated from animal tissues, may be produced by chemical synthesis, or may be produced by a plurality of these processes.

The fatty acid may be derived from natural sources, e.g., fish oils, or can be synthesized by methods as are known in the art. In some embodiments, the fatty acid may be contaminated with undesired components present in unrefined or unpurified natural products. In such situations, it can be desirable to remove undesired components, or to increase the concentration of desired components using known separation or purification techniques.

In any compound described, all tautomeric forms are also intended to be included. Without limitation, all tautomers of carboxylic groups are intended to be included.

In any compound described herein having one or more double bond(s) generating geometrical isomers that can be defined as E or Z, each double bond may independently be E or Z, or a mixture thereof.

Where compounds disclosed herein have unfilled valencies, then the valencies are to be filled with hydrogens or isotopes thereof, e.g., hydrogen-1 (protium) and hydrogen-2 (deuterium).

The fatty acid, such as an odd chain fatty acid or a very long even chain fatty acid, as described herein, includes crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The compounds described herein can be labeled isotopically. In some circumstances, substitution with isotopes such as deuterium may afford certain therapeutic advantages resulting from greater metabolic stability, such as, for example, increased in vivo half-life or reduced dosage requirements. Isotopic substitution may be beneficial in monitoring subject response to administration of a compound, for example, by providing opportunity for monitoring of the fate of an atom in a compound. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

The prevalence of various fatty acids in the diet has been correlated to the occurrence of metabolic syndrome in subjects (see, e.g., Forouhi N, Koulman A, Sharp S, Imamura F, Kröger J, Schulze M, et al. (2014), Differences in the prospective association between individual plasma phospholipid saturated fatty acids and incident type 2 diabetes: the EPIC-InterAct case-cohort study. Lancet Diabetes Endocrinol. 2:810-8). Indeed, whole-fat dairy consumption has been correlated with a decreased risk of metabolic syndrome markers (see, e.g., Kratz M, Marcovina S, Nelson J E, Yeh M M, Kowdley K V, Callahan H S, et al. (2014), Dairy fat intake is associated with glucose tolerance, hepatic and systemic insulin sensitivity, and liver fat but not beta-cell function in humans, Am. J. Clin. Nutr., 99:1385-96).

The mechanism(s) by which fatty acid(s) have a beneficial effect are not well understood. Without wishing to be limited by theory, it is thought that fatty acids, or derivatives thereof, can be elongated (increased in chain length) or chain shortened by metabolic processes in the body, to form different fatty acids, or derivatives thereof. Peroxidation of certain fatty acids may create products with signaling characteristics in the body. It is thought that fatty acids of certain chain length create signaling products that substantially contribute to one or more conditions provided herein. In some embodiments, an odd chain fatty acid is elongated to form a very long chain fatty acid, such as a very long even chain fatty acid. In further embodiments, a very long even chain fatty acid can be chain-shortened to an odd chain fatty acid. Levels of very long even chain fatty acids in the body may increase following administration of one or more odd chain fatty acids. Levels of odd chain fatty acids in the body may increase following administration of one or more very long even chain fatty acids.

Pharmaceutical Compositions Including One or More Fatty Acids

Formulations including a fatty acid, such as an odd chain fatty acid or a very long even chain fatty acid, or a salt or derivative thereof, and at least one excipient are provided. It is generally preferred to administer the compounds of the embodiments in oral formulations; however, other routes of administration are also contemplated.

The pharmaceutical compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The pharmaceutical compositions disclosed herein may be manufactured by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, a fatty acid, such as an odd chain fatty acid or a very long even chain fatty acid, or a salt or derivative thereof, may be combined as the active ingredient in intimate admixture with a pharmaceutical carrier according to conventional pharmaceutical compounding techniques. The carrier can take a wide variety of forms depending on the form of preparation desired for administration. Thus, the pharmaceutical compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion. In addition to the common dosage forms set out above, the compounds provided herein, or pharmaceutically acceptable salts or derivatives thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

A formulation may also be administered in a local rather than systemic manner, for example, via injection of the compound directly into the infected area, often in a depot or sustained release formulation. Furthermore, a targeted drug delivery system might be used, for example, in a liposome coated with a tissue specific antibody.

The pharmaceutical compositions may contain a fatty acid, such as an odd chain fatty acid or a very long even chain fatty acid, or a salt or derivative thereof, in an amount effective for the desired therapeutic effect. In some embodiments, the pharmaceutical compositions are in a unit dosage form and comprise from about 0.1 mg or less to about 5000 mg or more per unit dosage form. In further embodiments, the pharmaceutical compositions comprise from about 1 to about 500 mg per unit dosage form or from about 500 to 5000 mg per unit dosage form. Such dosage forms may be solid, semisolid, liquid, an emulsion, or adapted for delivery via aerosol or the like for inhalation administration.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

Pharmaceutical compositions provided herein can be prepared as solutions or suspensions of the active compound(s) in water. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Pharmaceutical compositions provided herein suitable for injectable use include sterile aqueous solutions or dispersions. Furthermore, the compositions can be in the form of sterile powders for the extemporaneous preparation of such sterile injectable solutions or dispersions. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound provided herein, or pharmaceutically acceptable salt or derivative thereof, can also be prepared in powder or liquid concentrate form for dilution.

The fatty acid, such as an odd chain fatty acid or a very long even chain fatty acid, or a salt or derivative thereof, can be formulated as a liposome. The fatty acid can be a component of the lipid portion of the liposome or can be encapsulated in the aqueous portion of the liposome. The fatty acid, such as an odd chain fatty acid or a very long even chain fatty acid, or a salt or derivative thereof, can also be coformulated with a cyclodextrin. The cyclodextrin can be, for example, hydroxypropyl-β-cyclodextrin or a sulfobutylether cyclodextrin.

Contemplated herein are compositions including a fatty acid, such as an odd chain fatty acid or a very long even chain fatty acid, or a salt or derivative thereof in combination with at least one additional active agent. A fatty acid, such as an odd chain fatty acid or a very long even chain fatty acid, or a salt or derivative thereof, and the at least one additional active agent(s) may be present in a single formulation or in multiple formulations provided together, or may be unformulated (for example, free of excipients and carriers). In some embodiments, a fatty acid, such as an odd chain fatty acid or a very long even chain fatty acid, or a salt or derivative thereof, can be administered with one or more additional agents together in a single composition. For example, a compound of a fatty acid, such as an odd chain fatty acid or a very long even chain fatty acid, or a salt or derivative thereof, can be administered in one composition, and at least one of the additional agents can be administered in a second composition. In a further embodiment, a fatty acid, such as an odd chain fatty acid or a very long even chain fatty acid, or a salt or derivative thereof and the at least one additional active agent(s) are co-packaged in a kit. For example, a drug manufacturer, a drug reseller, a physician, a compounding shop, or a pharmacist can provide a kit comprising a disclosed compound or product and another component for delivery to a patient.

Some embodiments described herein relate to a pharmaceutical composition, which can include a therapeutically effective amount of one or more compounds described herein (e.g., a fatty acid, such as an odd chain fatty acid or a very long even chain fatty acid, or a pharmaceutically acceptable salt or derivative thereof) and a pharmaceutically acceptable carrier, diluent, excipient or combination thereof. The pharmaceutical composition can include a fatty acid such as an odd chain fatty acid or a very long even chain fatty acid, or a salt or derivative thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. In some embodiments, the pharmaceutical composition can include a plurality of fatty acids, such as one or more of an odd chain fatty acid and/or a very long even chain fatty acid, or salts or derivatives thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

Formulations including a very long even chain fatty acid, or a salt or derivative thereof, and an odd chain fatty acid, or a salt or derivative thereof and at least one excipient are provided. It is generally preferred to administer the compounds of the embodiments in oral formulations; however, other routes of administration are also contemplated, as provided herein. In some embodiments, the pharmaceutical composition can include a very long even chain fatty acid and an odd chain fatty acid, or salts or derivatives thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition, e.g., from 1% to 98% of the composition, or any amount in between. A ratio of odd chain fatty acid, or a salt or derivative, to very long even chain fatty acid, or a salt or derivative, present in the formulation, on a weight basis, can be 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, or 95:5. In some embodiments, the fatty acids present in the formulation comprise 25% to 75% odd chain fatty acid(s), or salts or derivatives, with the remainder comprising very long even chain fatty acid(s), or salts or derivatives.

Foodstuffs

Foodstuffs and other comestibles including a fatty acid, such as an odd chain fatty acid or a very long even chain fatty acid, or a salt or derivative thereof, are provided, wherein an amount of the fatty acid in the foodstuff has been fortified (e.g., enriched or concentrated). A fatty acid, such as an odd chain fatty acid or a very long even chain fatty acid, provided herein may be added to foodstuffs for consumption by a subject. The fatty acid, such as an odd chain fatty acid or a very long even chain fatty acid, may be integrated into one or more ingredients of a foodstuff. The fatty acid, such as an odd chain fatty acid or a very long even chain fatty acid, may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic daily dosage of the fatty acid as described elsewhere herein; however, beneficial effects may also be obtained at amounts below such dosages.

A fatty acid, such as an odd chain fatty acid or a very long even chain fatty acid, or salt or derivative thereof, as provided herein may be present as a constituency in foodstuffs by operation of processes known in nature, for example, by altering the metabolic processes of a plant, animal, bacteria, or fungus. Genetic alteration of a plant, animal, bacteria, or fungus to increase the concentration of a fatty acid, such as an odd chain fatty acid or a very long even chain fatty acid, or a salt or derivative thereof, is contemplated. By way of example, the fatty acid can be present in the foodstuff in a concentration of at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%.

Indications

Provided are compositions and methods for treating inflammation and conditions related to inflammation. These conditions include but are not limited to anemia of chronic disease, insulin resistance, metabolic syndrome, hypertension, diabetes, nonalcoholic fatty liver disease, cardiovascular disease, cancer, diseases of aging, and neurodegenerative diseases, including Alzheimer's disease and other forms of dementia; metabolic syndrome and associated conditions (including diabetes type II, obesity, pre-diabetes, glucose intolerance, gestational diabetes mellitus (GDM), impaired fasting glycemia (IFG), impaired adiponectin production, postprandial hyperglycemia, dyslipidemia, post prandial dyslipidemia, hyperlipidemia, hypertriglyceridemia, post hypertriglyceridemia, insulin resistance, polycystic ovary syndrome (PCOS), non-alcoholic fatty liver disease (NAFLD), non-alcoholic steatohepatitis (NASH), hypoinsulinemia, fatty liver disease, elevated glucose levels, elevated insulin levels, elevated LDL-cholesterol levels, elevated triglyceride levels, low HDL-cholesterol levels, and dysmetabolic iron overload syndrome (DIOS)); hyperferritinemia and associated conditions (including infection, neoplasm, chronic or acute inflammation, autoimmune diseases, DIOS and other iron overload and iron storage disorders, Still's disease, idiopathic arthritis, hemophagocytic lymphohistiocytosis, macrophage activation syndrome, liver conditions including NAFLD NASH, and hepatocellular carcinoma, anemia of chronic inflammation, and neurodegenerative diseases, including Alzheimer's disease and other forms of dementia); and anemic disorders including, but not limited to hemolytic anemias (including but not limited to thalassemias, hereditary spherocytosis, hereditary elliptocytosis, glucose-6-phosphate dehydrogenase deficiency, pyruvate kinase deficiency, immune hemolytic anemia, alloimmune hemolytic anemia, drug-induced hemolytic anemia, mechanical hemolytic anemias, and paroxysmal nocturnal hemoglobinuria), anemia of chronic disease (wherein the underlying condition can be, for example, autoimmune disorders (such as, for example Crohn disease, systemic lupus erythematosus, rheumatoid arthritis, psoriasis, type 1 diabetes, multiple sclerosis, and ulcerative colitis), neoplastic disorders including cancer (such as, for example lymphoma, Hodgkin disease, and hepatocellular carcinoma), long-term infections (such as, for example bacterial, viral, and fungal infections), rheumatoid arthritis, ulcerative colitis, Hodgkin disease, metabolic syndrome, diabetes (for example, type 2 diabetes), and other causes of inflammation.

Aging refers to a series of morphological and functional changes in an organism which take place over time. The term also refers to the deterioration of the biological functions after an organism has attained its maximum reproductive potential. It is thought that inflammation may be related to aging through mutation to mitochondrial DNA and other processes.

Subjects suffering from a neurodegenerative condition, such as, for example, Alzheimer's disease, may display inflammation long before dementia is detected clinically. Amyloid beta, a peptide thought to be implicated in the development of neurodegenerative disease, may be correlated to inflammation and associated raised cytokines, which may in turn lead to neuron damage. Reducing inflammation may also protect neurons against amyloid beta toxicity. See Schmidt et al. (2002) Early inflammation and dementia: a 25-year follow-up of the Honolulu-Asia aging study. Ann Neurol 52:168-174 and Blasko et al. (2004) How inflammation can affect the brain and support the development of Alzheimer's disease in old age: the role of microglia and astrocytes. Aging Cell 3:169-176.

In some embodiments, the compositions and methods provided herein are indicated for treatment, prophylaxis, prevention or maintenance of a neurodegenerative disease. In variations of these embodiments, the disease is Alzheimer's disease. In further variations of these embodiments, the disease is Parkinson's disease. In still further variations of these embodiments, the disease is Huntington's disease or amyotrophic lateral sclerosis. In certain embodiments, a composition or method provided herein can reduce amyloid plaques.

Inflammation may contribute to hemolysis and anemia of chronic disease. Without wishing to be limited by theory, it is thought that red blood cells (RBCs) exposed to cytokines from inflammation undergo accelerated phagocytosis. In some embodiments, the compositions and methods provided herein are indicated for treatment, prophylaxis, prevention or maintenance of anemia of chronic disease.

Without wishing to be limited by theory, it is thought that increasing odd chain saturated fatty acid phospholipid levels in the serum, plasma, and cells may decrease inflammation. The resultant higher serum cholesterol esters or phospholipid odd chain saturated fatty acids independently predict lower inflammation.

In some embodiments, the compositions and methods provided herein are indicated for treatment, prophylaxis, prevention or maintenance of hyperferritinemia or a condition related thereto.

Ferritin is an important intracellular iron storage protein. Ferritin is thought to provide an accessible iron source for metabolic needs. Iron in the body can be found in hemoglobin in circulating RBCs, in developing erthyroblasts, in iron containing proteins, in transferring-bound iron, in ferritin, and in hemosiderin. The average human adult total body iron content is on the order of a few grams.

Hyperferritinemia is a blood condition involving high levels of serum ferritin. High ferritin can be a marker of iron overload. However, hyperferritinemia is also associated with a variety of systemic conditions including infection, neoplasm, chronic or acute inflammation, Still's disease, idiopathic arthritis, hemophagocytic lymphohistiocytosis, autoimmune diseases, metabolic syndrome, type 2 diabetes, macrophage activation syndrome, liver conditions including NAFLD, NASH, and hepatocellular carcinoma, anemia of chronic inflammation, and neurodegenerative diseases, including Alzheimer's disease and other forms of dementia. Elevated ferritin is also associated with inflammatory states, and can be considered an acute phase reactant. Inflammatory conditions associated with elevated ferritin include systemic lupus erythematosus, granulomatosis with polyangiitis, rheumatoid arthritis, scleroderma with pericarditis, inflammatory bowel disease, and graft-versus-host disease. Liver conditions associated with elevated ferritin include cirrhosis (for example, due to nonalcoholic steatohepatitis or primary biliary cirrhosis), autoimmune hepatitis, graft-versus-host disease, liver failure due to transient hypotension, toxin ingestion, alcoholic liver disease, nonalcoholic steatohepatitits, viral hepatitis, and acute liver injury. In some instances, hyperferritinemia may have no apparent cause.

An anemic condition can be classified as normochromic, which is generally understood to be an anemic condition in which the concentration of hemoglobin in the RBCs is not pathological, but there are insufficient numbers of RBCs. An anemic condition can be classified as normocytic, which is generally understood to be an anemic condition in which RBCs are not abnormal in size. Normocytic, normochromic anemias include anemia of chronic disease (ACD) and hemolytic anemia.

RBCs can be removed from circulation due to senescence. Without wishing to be bound by theory, RBCs undergo age-dependent alterations, which may include a decline in metabolic activity, a progressive cell shape transformation, membrane remodelling, oxidative injury, microvesiculation and exposure of surface removal markers. These modifications may trigger phagocytosis by macrophages, in which RBCs are destroyed. It is thought that the protease calpain may become activated in the process, which may be triggered by an increase of cytosolic calcium. Elevated rates of RBC destruction may lead to an anemic condition.

Anemia of chronic disease (ACD), also called anemia of inflammation and inflammatory anemia, is anemia associated with a chronic underlying condition. An underlying condition may suppress production of red blood cells in the bone marrow, may decrease the lifespan of red blood cells, or may create problems with how the body uses iron. Generally, ACD develops and presents slowly, with mild or no symptoms.

Inflammation may play a role in the pathogenesis of ACD. Without wishing to be bound by theory, it is thought that inflammatory cytokines present in many chronic diseases, which both lower red blood cell production and raise premature breakdown of senescent cells, leading to anemia. Thus, cytokines and cells of the reticuloendothelial system affect iron homeostasis, production of erythroid progenitor cells, the production of erythropoietin, and the life span of RBCs, each of which can contribute to an anemic condition. Further, ACD may be associated with abnormal homeostasis of iron in the body. Increased uptake and retention of iron within cells of the reticuloendothelial system may be observed. In subjects having ACD, ferritin levels may be elevated.

In some embodiments provided herein, the subject may be a dolphin; however, it is generally contemplated that the methods, uses, and compositions of the embodiments are applied to humans. Like human subjects, bottlenose dolphin (*Tursiops truncatus*) subjects can also be susceptible to anemia, and to metabolic syndrome, including high insulin, glucose, triglycerides, fatty liver disease, and iron overload. Iron overload in dolphins, involving excessive iron deposition primarily in the liver's Kupffer cells, can be progressive with age and can be associated with elevated insulin, lipids, and liver enzymes. This disease is associated with neither mutations in the HFE gene nor increases in studied acute phase proteins. Similar to humans, iron overload in dolphins have in the past been treated with phlebotomy, and repeated treatments are needed throughout life due to returning elevations of serum ferritin. The underlying causes of iron overload and hyperferritinemia in dolphins are unknown.

In some embodiments, the condition treated is inflammation.

In some embodiments, the condition treated is inflammation as indicated by the markers provided herein.

In some embodiments, the methods provided herein modulate markers of inflammation components when the markers provide a clinical indication.

In some embodiments, the methods provided herein alleviate symptoms of inflammation.

In some embodiments, the methods provided herein reduce risk of inflammation.

In some embodiments, the methods provided herein increase levels of serum, plasma, or erythrocyte membrane odd chain fatty acids.

In some embodiments, the methods provided herein increase levels of serum, plasma, or erythrocyte membrane very long even chain fatty acids. In further embodiments, levels of serum, plasma, or erythrocyte membrane very long even chain fatty acids may increase following administration of one or more odd chain fatty acids, or a salt or derivative thereof.

In some embodiments, the condition treated is anemia of chronic disease.

In some embodiments, the condition treated is autoimmune disease.

In some embodiments, the methods provided herein increase levels of serum very long even chain fatty acids.

In some embodiments, the compositions and methods provided herein modulate a marker of inflammation. In certain embodiments, the marker is serum, plasma, or red blood cell membrane odd chain fatty acid percentage; serum, plasma, or red blood cell membrane concentration of an odd chain fatty acid; serum plasma, or red blood cell membrane total odd chain fatty acid; erythrocyte sedimentation rate, alkaline phosphatase, serum ferritin, CRP (C reactive protein), IL-6 and TNFα (and other cytokines associated with insulin resistance), c-Jun N-terminal kinase (JNK), ATM (Ataxia Telangiectasia Mutated) or monocyte-chemoattractant protein-1. In some embodiments, the odd chain fatty acid is measured as a constituent of glycolipids. In further embodiments, the odd chain fatty acid is measured as a constituent of phospholipids. In still further embodiments, the marker is serum or red blood cell membrane very long even chain fatty acid percentage, serum concentration of a very long even chain fatty acid, serum total very long even chain fatty acids.

In some embodiments, the methods provided herein include the step of measuring the concentration of a marker of inflammation. One of skill in the art will be able to perform suitable methods for such measurements, including but not limited to those described herein.

Provided herein are methods for treating including the step of administering a dose of a fatty acid, such as an odd chain fatty acid or a very long even chain fatty acid, at a predetermined interval, or at an interval left to the discretion of the subject.

In some embodiments, the compounds and methods provided herein may provide a threshold serum, plasma, or red blood cell membrane percentage of an odd chain fatty acid relative to all serum, plasma, or red blood cell membrane fatty acids, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum or plasma concentration of an odd chain fatty acid, or red blood cell membrane concentration of an odd chain fatty acid. For example, a serum or plasma odd chain fatty acid or red blood cell membrane concentration of an odd chain fatty acid may be increased by at least about 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, or more than 50 µg/ml. In some embodiments, the serum concentration of an odd chain fatty acid, or red blood cell membrane concentration of an odd chain fatty acid may increase above a baseline value (e.g., pretreatment value in a patient being treated, or general value observed in a particular patient population) by at least about $0.01\times10^{-4}$ M, at least about $0.05\times10^{-4}$ M, at least about $0.1\times10^{-4}$ M, at least about $0.2\times10^{-4}$ M, at least about $0.3\times10^{-4}$ M, at least about $0.4\times10^{-4}$ M, at least about $0.5\times10^{-4}$ M, at least about $0.6\times10^{-4}$ M, at least about $0.7\times10^{-4}$ M, at least about $0.8\times10^{-4}$ M, at least about $0.9\times10^{-4}$ M, at least about $1\times10^{-4}$ M, at least about $2\times10^{-4}$ M, or at least about $3\times10^{-4}$ M.

In some embodiments, the compounds and methods provided herein may provide an increase in serum or plasma total odd chain fatty acids, or red blood cell membrane total odd chain fatty acids. For example, serum total odd chain fatty acids, or red blood cell membrane total odd chain fatty acids, may be increased above a baseline value (e.g., pretreatment value in a patient being treated, or general value observed in a particular patient population) by at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, the compounds and methods provided herein may provide an increase above a baseline value (e.g., pretreatment value in a patient being treated, or general value observed in a particular patient population) in a serum, plasma, or red blood cell membrane odd chain fatty acids relative to all serum or red blood cell membrane fatty acids, respectively. For example, a serum, plasma, or red blood cell membrane odd chain fatty acid may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, or more than 5%.

In some embodiments, the compounds and methods provided herein may provide a reduction in elevated erythrocyte sedimentation rate.

In some embodiments, the compounds and methods provided herein may provide a reduction in elevated alkaline phosphatase.

In some embodiments, the compounds and methods provided herein may provide a reduction in serum ferritin. For example, serum ferritin may be reduced below a baseline value (e.g., pretreatment value in a patient being treated, or general value observed in a particular patient population) by at least about 10 ng/ml, at least about 100 ng/ml, at least about 200 ng/ml, at least about 300 ng/ml, at least about 400 ng/ml, at least about 500 ng/ml, at least about 600 ng/ml, at least about 700 ng/ml, at least about 800 ng/ml, at least about 900 ng/ml, at least about 1000 ng/ml, at least about 1100 ng/ml, at least about 1200 ng/ml, at least about 1300 ng/ml, at least about 1400 ng/ml, at least about 1500 ng/ml, at least about 2000 ng/ml, at least about 2500 ng/ml, at least about 3000 ng/ml, at least about 3500 ng/ml, at least about 4000 ng/ml, at least about 4500 ng/ml, at least about 5000 ng/ml, at least about 6000 ng/ml, at least about 7000 ng/ml, at least about 8000 ng/ml, at least about 9000 ng/ml, at least about 10000 ng/ml, or more than 10000 ng/ml.

In some embodiments, the compounds and methods provided herein may provide a reduction in serum ferritin below a specified level. For example, serum ferritin may be reduced below about 20000 ng/ml, about 15000 ng/ml, about 12000 ng/ml, about 10000 ng/ml, about 8000 ng/ml, about 5000 ng/ml, about 2000 ng/ml, about 1000 ng/ml, or about 500 ng In some embodiments, an odd chain fatty acid is administered to maintain serum or plasma total percent of the odd chain fatty acid, or all odd chain fatty acids, above a predetermined threshold value. In variations of these embodiments, the odd chain fatty acid is heptadecanoic acid. In further variations, the odd chain fatty acid is administered to maintain serum phospholipid percent of the odd chain fatty acid, or all odd chain fatty acids, above about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2%, about 2.2%, about 2.4%, or about 2.6%.

In some embodiments, the compounds and methods provided herein may provide a threshold serum, plasma, or red blood cell membrane percentage of a very long even chain fatty acid relative to all serum or red blood cell membrane fatty acids, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum or plasma concentration of a very long even chain fatty acid, or red blood cell membrane concentration of a very long even chain fatty acid. For example, a serum very long even chain fatty acid or red blood cell membrane concentration of a very long even chain fatty acid may be increased by at least about 0.01 µg/ml, at least about 0.05 µg/ml, at least about 0.1 µg/ml, at least about 0.4 µg/ml, 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, or more than 50 µg/ml. In some embodiments, the serum concentration of a very long even chain fatty acid, or red blood cell membrane concentration of a very long even chain fatty acid may increase above a baseline value (e.g., pretreatment value in a patient being treated, or general value observed in a particular patient population) by at least about $0.001 \times 10^{-4}$ M, at least about $0.005 \times 10^{-4}$ M, at least about $0.05 \times 10^{-4}$ M, at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum or plasma total very long even chain fatty acids, or red blood cell membrane total very long even chain fatty acids. For example, serum total very long even chain fatty acids, or red blood cell membrane total very long even chain fatty acids, may be increased above a baseline value (e.g., pretreatment value in a patient being treated, or general value observed in a particular patient population) by at least about 0.05 µg/ml, at least about 0.1 µg/ml, at least about 0.5 µg/ml, at least about 1 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, the compounds and methods provided herein may provide an increase above a baseline value (e.g., pretreatment value in a patient being treated, or general value observed in a particular patient population) in a serum, plasma or red blood cell membrane very long even chain fatty acids relative to all serum, plasma or red blood cell membrane fatty acids, respectively. For example, a serum or red blood cell membrane very long even chain fatty acid may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, or more than 5%.

In some embodiments, a very long even chain fatty acid is administered to maintain serum or plasma phospholipid percent of the very long even chain fatty acid, or all very long even chain fatty acids, above a predetermined threshold value. In variations of these embodiments, the very long even chain fatty acid is behenic acid. In further variations, the very long even chain fatty acid is administered to maintain serum phospholipid percent of the very long even chain fatty acid, or all very long even chain fatty acids, above about 0.1%, about 0.2%, about 0.3%, about 0.4%, about 0.5%, about 0.6%, about 0.7%, about 0.8%, about 0.9%, about 1%, about 1.2%, about 1.4%, about 1.6%, about 1.8%, about 2%, about 2.2%, about 2.4%, or about 2.6%.

In some embodiments, a composition or method provided herein may provide an increase in red blood cell count. For example, a red blood cell count level may be increased above a baseline value (e.g., pretreatment value in a patient being treated, or general value observed in a particular patient population) by at least about 0.1 cells/µL, at least about 0.2 cells/µL, at least about 0.3 cells/µL, at least about 0.4 cells/µL, at least about 0.5 cells/µL, at least about 0.6 cells/µL, at least about 0.7 cells/µL, at least about 0.8 cells/µL, at least about 0.9 cells/µL, at least about 1 cell/µL, at least about 1.2 cells/µL, at least about 1.4 cells/µL, at least about 1.6 cells/µL, or at least about 2 cells/µL.

Combination Therapies

In some embodiments, the compounds disclosed herein, such as an odd chain fatty acid, or a salt or derivative thereof, or a very long even chain fatty acid, or a salt or derivative thereof, or a pharmaceutical composition that includes a compound described herein, or a salt or derivative thereof, may be used in combination with one or more additional active agents. Examples of additional active agents that can be used in combination with a compound of an odd chain fatty acid or a very long even chain fatty acid, or a salt or derivative thereof, or a composition that includes a compound of an odd chain fatty acid, or a salt or derivative thereof, a very long even chain fatty acid, or a salt or derivative thereof, include, but are not limited to, agents currently used for treating conditions provided herein, and as otherwise known to medical science.

In some embodiments, a compound of an odd chain fatty acid, or a salt or derivative thereof, a very long even chain fatty acid, or a salt or derivative thereof, or a composition that includes a compound of an odd chain fatty acid, or a salt or derivative thereof, a very long even chain fatty acid, or a salt or derivative thereof, can be used with one, two, three or more additional active agents described herein. Such agents include, but are not limited to, a second fatty acid, such as an odd chain fatty acid or a very long even chain fatty acid, or a salt or derivative thereof. In some embodiments, a composition can include at least one odd chain fatty acid, or a salt or derivative thereof, and at least one very long even chain fatty acid, or a salt or derivative thereof.

In some embodiments, a compound of an odd chain fatty acid, or a salt or derivative thereof, a very long even chain fatty acid, or a salt or derivative thereof, or a composition that includes a compound of an odd chain fatty acid, or a salt or derivative thereof, a very long even chain fatty acid, or a salt or derivative thereof, can be used (for example, administered or ingested) in combination with another agent or agents for treatment, prevention, maintenance, or prophylaxis of a condition provided herein including metabolic syndrome, hyperferritinemia, inflammation, a condition of oxidative stress, or an anemic condition, or for modulation of markers of the condition. In some embodiments, the condition can be an anemic condition selected from hemolytic anemias (including but not limited to thalassemias, hereditary spherocytosis, hereditary elliptocytosis, glucose-6-phosphate dehydrogenase deficiency, pyruvate kinase deficiency, immune hemolytic anemia, alloimmune hemolytic anemia, drug-induced hemolytic anemia, mechanical hemolytic anemias, and paroxysmal nocturnal hemoglobinuria), anemia of chronic disease (wherein the underlying condition can be, for example, autoimmune disorders (such as, for example Crohn disease, systemic lupus erythematosus, rheumatoid arthritis, type 1 diabetes, and ulcerative colitis), neoplastic disorders including cancer (such as, for example lymphoma and Hodgkin disease), long-term infections (such as, for example bacterial, viral, and fungal infections), rheumatoid arthritis, ulcerative colitis, Hodgkin disease, metabolic syndrome, diabetes (for example, type 2 diabetes), and other causes of inflammation), anemia, aplastic anemias (including but not limited to congenital hypoplastic anemia, Diamond-Blackfan anemia and Fanconi anemia), iron deficiency anemia, anemias of abnormal RBC size (including but not limited to megaloblastic anemia and microcytic anemia), vitamin deficiency anemias (including but not limited to pernicious anemia) anemia of RBC mutation (including but not limited to thalassemia, sideroblastic anemia and sickle cell anemia). For example, a compound of a fatty acid, such as an odd chain fatty acid or a very long even chain fatty acid, disclosed herein can be used in combination with one or more agents selected from iron chelators, albiglutide, aleglitazar, balaglitazone, canagliflozin, CJ-30001 (CJ Cheiljedang Corporation), CJ-30002 (CJ Cheiljedang Corporation), Diamyd® (glutamic acid decarboxylase (rhGAD65)), dulaglutide, exendin 4, gemigliptin, lixisenatide, lobeglitazone, shengke I (Tibet Pharmaceuticals), SK-0403 (Sanwa Kagaku Kenkyusho), teneligliptin, teplizumab, tofogliflozin, acarbose, alogliptin benzoate, chlorpropamide, Diab II (Biotech Holdings), exenatide, glibenclamide, gliclazide, glimepiride, glipizide, gliquidone, glisentide, glisolamide, HL-002 (HanAII Biopharma), insulin (human), insulin, insulin analogue (Eli Lilly®), insulin aspart, insulin detemir, insulin glargine, insulin lispro, Janumet®, linagliptin, liraglutide, metformin, miglitol, mitiglinide, nateglinide, Novo Mix 30® (Novo Nordisk®) pioglitazone, pramlintide, repaglinide, rosiglitazone maleate, saxagliptin, sitagliptin, Tresiba, tolazamide, tolbutamide, vildagliptin, voglibose, bezafibrate, diflunisal, cinnamic acid, carbutamide, glyburide (glibenclamide), glibomuride, glyhexamide, phenbutamide, and tolcyclamide or with one or more agents selected from a class of agents, where the classes include sulfonylureas, non-sulfonylurea secretagogues, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adeno sine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diguanides, diuretics, dopamine D1 receptor agonists, endopeptidase inhibitors, endothelin receptor antagonists, guanylate cyclase stimulants, phosphodiderivativease V inhibitors, protein kinase inhibitors, Cdc2 kinase inhibitors, renin inhibitors, thromboxane synthase inhibitors, vasopeptidase inhibitors, vasopressin 1 antagonists, vasopressin 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholderivativeyl derivative transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipoprotein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists lipase inhibitors, melanin-concentrating hormone receptor antagonists, nerve growth factor agonists, neuropeptide Y agonists, neuropeptide Y antagonists, SNRIs, protein tyrosine phosphatase inhibitors, serotonin 2C receptor agonists, or with other agents such as central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), dopamine antagonists, cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, α-melanocyte-stimulating hormone analogues, melanocoritin-4 receptor agonists, and agents that affect insulin metabolism/activity, which include protein-tyrosine phosphatase-IB inhibitors, peroxisome proliferator activated receptor-.gamma. receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion; or with one or more agents selected from ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-1 13715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1 D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; β-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPYSRA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB 1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; PPAR pan agonists; EP-01492; hormone- sensitive lipase inhibitors; fatty acid-binding protein 4 inhibitors; thiolactone derivatives; protein tyrosine phosphatase IB inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; angiogenesis inhibitors; G protein-coupled receptor agonists; nicotinic therapeutics (ChemGenex); anti-obesity agents (Abbott); melanin concentrating hormone; GW-594884A; MC-4R agonist; histamine H3 antagonists; orphan GPCR modulators; MITO-3108; NLC-002; HE-2300; IGF/BBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; beta-3 adrenoceptor agonists; ob gene products (Eli Lilly & Co.); SWR-0342-SA; SWR-0335; SP-18904; oral insulin mimetics; obesity therapeutics (7TM Pharma); beta-hydroxysteroid dehydrogenase (HSD) inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; PY-1 antagonists; A-71378; ®-didesmethylsi-butramine; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BDBP-3226; HP-228; talibegron; FR-165914; AZM-008; AZM-016; AZM-120; AZM-090; AZM-131; AZM-132; AZM-134; AZM-127; AZM-083; AZM-1 15; AZM-140; vomeropherin; BMS-187257; D-3800; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; exopipam; SSR-125180; obesity therapeutics (Melacure Therapeutics AB); BRL-35135; SR-146131; P-57; CGP-71583A; RF-1051; BMS-196085; manifaxine; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; AOD-9604; ATL-062; BVT-933; GT389-255; SLV319; HE-2500; PEG-axokine; L-796568; and ABT-239; rimonabant, sibutramine, orlistat, PYY or an analog thereof, CB-1 antagonist, leptin, phentermine, and exendin analogs; GPR1 19 agonists (e.g., anandamide; AR-231, 453; MBX-2982; Oleoylethanolamide; PSN-365,963; PSN-632,408; palmitoylethanolamide); GPR120 agonists; GPR 40 agonists; and SGLT2 inhibitors.

Additionally, a fatty acid or salt or derivative as provided herein can be used in combination with one or more agents selected from Altoprev (lovastatin), Crestor (rosuvastatin), Lescol (fluvastatin), Lipitor (atorvastatin), Livalo (pitavastatin), Pravachol (pravastatin), Zocor (simvastatin), an anti-platelet medication, a beta blocker, an ACE inhibitor, a calcium channel blocker, a diuretic, anticoagulants, aspirin, bile acid sequestrants, Ezetimibe, Fibrates, Glycoprotein IIb/IIIa Receptor Inhibitors, Niacin (Nicotinic Acid), Nitrates, Platelet Inhibitors, Thrombolytics, lisinopril oral, atenolol oral, Bystolic oral, Diovan oral, hydrochlorothiazide oral, metoprolol succinate oral, amlodipine oral, Norvasc oral, Toprol XL oral, Benicar oral, metoprolol tartrate oral, losartan oral, lisinopril-hydrochlorothiazide oral, clonidine HCl oral, Diovan HCT oral, Cozaar oral, propranolol oral, spironolactone oral, Azor oral, carvedilol oral, Coreg oral, Benicar HCT oral, Exforge oral, Avapro oral, Lotrel oral, verapamil oral, furosemide oral, Lasix oral, Hyzaar oral, Tekturna oral, enalapril maleate oral, Micardis oral, losartan-hydrochlorothiazide oral, ramipril oral, Lopressor oral, Altace oral, Micardis HCT oral, Avalide oral, diltiazem oral, triamterene-hydrochlorothiazide oral, labetalol oral, terazosin oral, amlodipine-benazepril oral, hydralazine oral, Atacand oral, benazepril oral, Tribenzor oral, triamterene oral, doxazosin oral, nifedipine oral, Ziac oral, Aldactone oral, Maxzide oral, Cartia XT oral, prazosin oral, Cardizem CD oral, Zestril oral, Dyazide oral, bisoprolol fumarate oral, Tenex oral, Tenormin oral, Coreg CR oral, Prinivil oral, valsartan oral, atenolol-chlorthalidone oral, Edarbyclor oral, benazepril-hydrochlorothiazide oral, ferrous sulfate oral, Ferrlecit intravenous, Feraheme intravenous, Feosol oral, Infed injection, Integra oral, Ferrex 150 Forte oral, Tandem Dual Action oral, Ferrex 150 oral, ferrous gluconate oral, Corvite 150 oral, Integra F oral, NovaFerrum oral, Iron (ferrous sulfate) oral, Vitron-C oral, Folic acid, corticosteroids, rituximab, IVIG, prednisone, methylprednisolone oral, Kenalog injection, Medrol (Pak) oral, Medrol oral, dexamethasone oral, Depo-Medrol injection, prednisolone oral, DexPak 13 Day oral, Solu-Medrol intravenous, hydrocortisone oral, Cortef oral, Deltasone oral, triamcinolone acetonide injection, cortisone oral, cholinesterase inhibitors such as Donepezil (Aricept), Rivastigmine (Exelon), and Galantamine (Razadyne), Memantine, Aricept, Namenda, Namenda XR, Razadyne ER, Alpha E, vitamin E, Hydergine, Namzaric, Dopamine Agonists such as pramipexole (Mirapex), ropinirole (Requip), rotigotine (Neupro patch) and apomorphine (Apokyn), Anticholinergics such as benztropine (Cogentin) and trihexyphenidyl, MAO-B Inhibitors such as (Eldepryl, Zelapar) and rasagiline (Azilect), COMT Inhibitors such as Entacapone (Comtan), Carbidopa/Levodopa (Sinemet®), amantadine, Tetrabenazine (Xenazine), haloperidol (Haldol), chlorpromazine, risperidone (Risperdal), quetiapine (Seroquel), olanzapine (Zyprexa), indomethacin, sulindac, etodolac, mefenamic acid, meclofenamic acid, meclofenamate sodium, flufenamic acid, tolmetin, ketorolac, diclofenac, diclofenac sodium, ibuprofen, naproxen, naproxen sodium, fenoprofen, ketoprofen, flurbiprofen, oxaprozin piroxicam, meloxicam, ampiroxicam, droxicam, lornoxicam, cinnoxicam, sudoxicam, and tenoxicam.

Additionally, a compound of a fatty acid disclosed herein can be used in combination with one or more agents selected from iron dextran, iron sumalate, polysaccharide iron, ferrus fumarate, carbonyl iron, ferrous asparto glycinate, heme iron polypeptide can be sometimes indicated, ferrus bisglycinate as can be the administration of other medicaments such as androgen hormones, such as erythropoietin, folic acid, vitamin B12, vitamin C, succinic acid, niacin, pyridoxine, riboflavin, biotin, thiamine, calcium formate, Aminoxin, Anadrol-50, Chromagen Forte, Epoetin alfa, Epogen, Fe C Tab Plus, FeRiva, FeRivaFA, Ferocon, Ferotrin, Ferralet 90, Ferrex 28, Ferrogels Forte, FoliTab 500, Fumatinic, Hematogen Forte, Hemetab, Integra Plus, Irospan 42/6, Lenalidomide, Maxaron Forte, Myferon 150 Forte, MyKidz Iron, NovaFerrum, Oxymetholone, Procrit, Proferrin-Forte, Pyridoxine, Repliva 21/7, Revlimid, and Tricon.

Dosing

As will be readily apparent to one skilled in the art, the useful in vivo dosage to be administered and the particular mode of administration will vary depending upon the age, weight, the severity of the condition, and mammalian species treated, the particular forms of the compounds employed, and the specific use for which these compounds are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein. In some embodiments, a therapeutically effective amount may be determined by reference to the modulation of a marker of a condition provided herein including inflammation. In some embodiments, a therapeutically effective amount may be determined by reference to the modulation of a symptom of a condition provided herein. In still other embodiments, reference may be made to established guidelines for the conditions described herein, including, but not limited to, guidelines for the treatment of a condition provided herein including inflammmation.

The dosage may vary broadly, depending upon the desired effects and the therapeutic indication, such as marker values. Alternatively, dosages may be based and calculated upon the surface area or weight of the patient, as understood by those of skill in the art. The exact dosage will be determined on a case-by-case basis, or, in some cases, will be left to the informed discretion of the subject. The daily dosage regimen for an adult human patient may be, for example, an oral dose of a fatty acid, such as an odd chain fatty acid or a very long even chain fatty acid, or a salt or derivative thereof, or a mixture of a plurality of fatty acids, or a salt or derivative thereof, from about 0.01 mg to about 10000 mg, from about 1 mg to about 5000 mg, from about 5 mg to about 2000 mg, from about 10 mg to about 1000 mg, or from about 50 mg to about 500 mg. A single dose may include a fatty acid, or a salt or derivative thereof, in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more. The dosage may be adjusted according to the body mass of the subject, for example, the dosage may be about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher. The dosage may be a single one or a series of two or more given in the course of one or more days, as is appropriate for the individual subject. In some embodiments, the compounds will be administered for a period of continuous therapy, for example for about a week or more (e.g., one week, two weeks, three weeks, four weeks, five weeks, six weeks, seven weeks, eight weeks, or more), for several weeks, for about a month or more (e.g., one month, two months, three months, four months, five months, six months, seven months, eight months, nine months, ten months, eleven months, twelve months, or more), for about a year or more, or for a plurality of years. In some embodiments, a fatty acid, such as an odd chain fatty acid or a very long even chain fatty acid, or a salt or derivative thereof, can be administered or ingested one time per day, two times per day, three times per day, or more.

As will be understood by those of skill in the art, in certain situations it may be necessary to administer the compounds disclosed herein in amounts that exceed the above-stated, preferred dosage range in order to effectively treat a subject.

Unit dosage forms can also be provided, e.g., individual packages with a premeasured amount of the composition, configured for administration on a predetermined schedule. Unit dosage forms configured for administration one to three times a day are preferred; however, in certain embodiments it may be desirable to configure the unit dosage form for administration more than three times a day, or less than one time per day.

Dosage amount and interval may be adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

In some embodiments, the compounds and methods provided herein may be used in conjunction with devices and methods of using devices, for example, as provided in U.S. Pat. Nos. 7,651,845; 8,251,904; 8,251,904; 4,985,015; 8,827,957; 4,252,159; 5,318,521; 4,718,430; U.S. 2011/0190702; DE2615061; and in conjunction with diagnostic devices, for example, as provided in U.S. 2012/0072236.

Diagnosis and Monitoring

Provided herein are methods for the diagnosis and monitoring of conditions provided herein including inflammation.

In some embodiments, the method of diagnosis or monitoring may comprise the step of measuring a percentage of a fatty acid, such as an odd chain fatty acid or a very long even chain fatty acid, in a bodily fluid. In some embodiments, the method of diagnosis or monitoring may comprise the step of measuring a marker of a condition provided herein including inflammation in a subject. In some embodiments, the method of diagnosis or monitoring may comprise the step of measuring a marker of anemia of chronic disease. In some embodiments, a correlation between one marker and another may prove instructive. In some embodiments, inflammation or a related condition may be diagnosed by reference to a threshold level of erythrocyte sedimentation rate, for example, or serum odd chain fatty acid or serum very long even chain fatty acid. In some embodiments, a condition provided herein including inflammation may be diagnosed by reference to a threshold level of a marker of the condition, for example, serum odd chain fatty acid percentage, serum concentration of an odd chain fatty acid, serum total odd chain fatty acid, serum very long even chain fatty acid, serum total very long even chain fatty acids, or a ratio between two serum fatty acids. For example, the threshold may be determined by reference to a symptom or marker of a condition provided herein including inflammation. For example, the condition can be metabolic syndrome.

The percentage of a fatty acid, such as an odd chain fatty acid or a very long even chain fatty acid, or a marker of a condition provided herein including inflammation, in a subject may be monitored by any means. Samples for analysis may be derived any fluid or tissue of the subject. For example, from serum, plasma, erythrocyte membranes, urine, and feces.

EXAMPLES

Example 1

Dolphins at the Navy Marine Mammal Program (MMP) are a well-studied dolphin population with regard to chronic diseases and diseases of aging, including metabolic syndrome and iron dysmetabolic diseases, and this population is susceptible to inflammation, especially with age (see Venn-Watson S, Smith C R, Gomez F, Jensen E D (2011) Physiology of aging among healthy, older bottlenose dolphins (*Tursiops truncatus*): comparisons with aging humans. *J Comp Phys B* 181:667-680).). MMP dolphins have a higher susceptibility to metabolic syndrome, insulin resistance, and iron storage diseases compared to wild dolphins living in Sarasota Bay dolphins (see Venn-Watson et al. (2016) Increased dietary intake of saturated fatty acid heptadecanoic acid (C17:0) associated with decreasing ferritin and alleviated metabolic syndrome in dolphins. PLOS ONE 10(7):e0132117). MMP dolphins also have lower total serum odd chain saturated fatty acid levels and lower very long even chain saturated fatty acid levels compared to Sarasota Bay dolphins (Table 1), Proposed risk factors for inflammation in MMP dolphins can include advanced age, chronic disease, and diet. It can be hypothesized that differences in dietary fish (and differences in certain fatty acids associated with particular types of fish) can be responsible for the risk of inflammation.

This study examined the impact on inflammation by modifying fatty acid profiles through the diet in 20 MMP dolphins ("Group A dolphins"). The dolphins lived in netted enclosures within San Diego Bay. The diets of the 20 Group A dolphins were modified from a 75% capelin (plus 25% mix of squid, herring or mackerel) baseline diet to a diet consisting of 25% capelin, 50% mullet, and 25% mix of squid, herring, or mackerel while maintaining the same kilocalories. On blood collection days, Group A dolphins were fed one-third of their daily diet in the morning after their routine overnight fast and 2h postprandial, in-water, and trained blood samples were drawn (typically near 10:00 a.m.). An additional ten MMP dolphins ("Group B dolphins") were maintained on the baseline capelin diet throughout the study period. There were no differences in age, sex, or body weight when comparing the two groups (Table 2).

Capelin, the primary baseline fish type fed to MMP dolphins, had no detectable C17:0 (<0.007 g/100 g). Mullet, the primary fish type fed in the modified diet, had 67 mg/100 g of C17:0. For other fish, C17:0 was measured as follows: herring=19 mg/100 g, and mackerel=22 mg/100 g. There was no detectable C17:0 in squid (See also Venn-Watson et al. (2016) Increased dietary intake of saturated fatty acid heptadecanoic acid (C17:0) associated with decreasing ferritin and alleviated metabolic syndrome in dolphins. PLOS ONE 10(7):e0132117).

Comparisons of daily fatty acid intake of the dolphins' baseline and modified diets are provided (Table 3), including demonstrated increased intake of odd chain saturated fatty acids C17:0 from a daily mean of 300 to 1,100 mg (approximately a four-fold increase) and C15:0 from a daily mean of 1,300 to 4,500 mg (approximately a three-fold increase). The very long even chain saturated fatty acid, C24:0, increased from a daily mean intake of 0 to 300 mg. Given an approximate average body weight of study dolphins of 159 kg, the modified diet provided an approximate daily oral dose of C15:0 at 28 mg/kg body weight. The modified approximate daily oral dose of C17:0 was 7 mg/kg body weight. The modified approximate daily oral dose of C24:0 was 1.9 mg/kg body weight. When comparing the modified and baseline diets, there were no changes in total fat intake, C18:0 or C22:0. Daily intake of the even chain fatty acids C14:0, C16:0, and C20:0, as well as total omega 3, total polyunsaturated, and total saturated fats decreased on the modified diet.

Two hour post-prandial samples were collected from Group A and Group B dolphins at baseline (month 0) and at three time points following the switch to the modified diet: months 1, 3, and 6. Dolphins were assessed for changes in serum fatty acid concentrations (total and various forms) and indices of inflammation, including erythrocyte sedimentation rate and alkaline phosphatase.

Figure 1B:
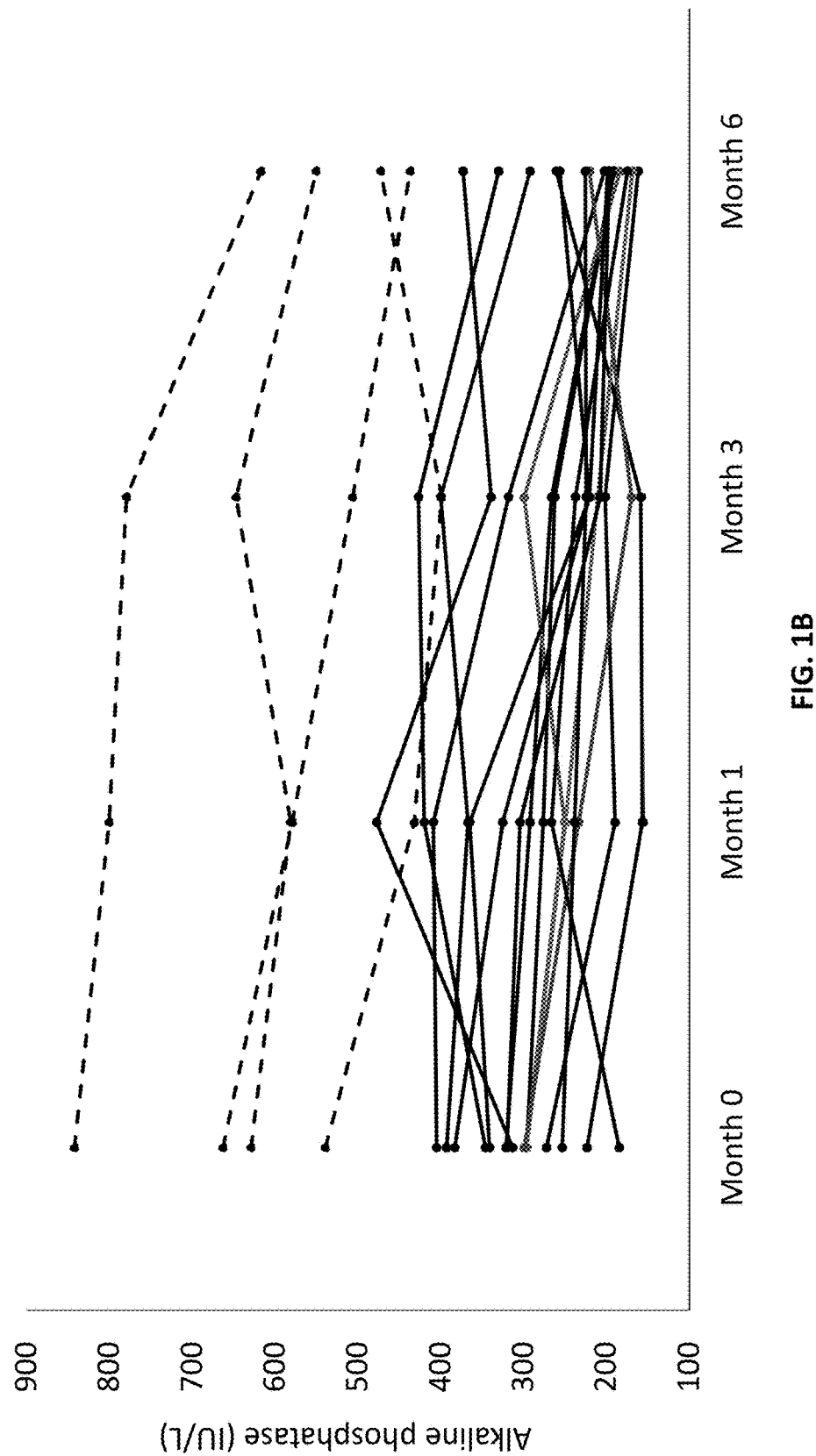

Changes in serum fatty acid concentrations, including odd chain saturated fatty acids and very long even chain saturated fatty acids, as well as erythrocyte sedimentation rate and alkaline phosphatase, were compared in study dolphins during months 1, 3, and 6 and compared to month 0 using repeated measures ANOVA. Outcomes for markers of anemia for Group A and Group B dolphins are provided in Table 4. Erythrocyte sedimentation rate was lowered in Group A dolphins by Month 1 and through Month 6. Alkaline phosphatase was lowered in Group A dolphins by Month 3 and through Month 6. These changes were not present in Group B dolphins. It is apparent in FIGS. 1A-1B that individual Group A dolphins with high erythrocyte sedimentation rate had resolving inflammation while on the modified diet.

When the modified diet adding 50% mullet was fed to 20 Group A dolphins over 6 months (increasing the average daily dietary C17:0 intake from 300 to 1100 mg and C15:0 daily intake from 1,300 to 4,500 mg), total serum odd chain saturated fatty acid concentrations increased by Month 1 compared to Month 0 and maintained increased serum concentrations throughout the six months (Table 5). Specifically, at Month 1, serum total C15:0 concentrations increased to 94±33 uM, and serum total C17:0 concentrations increased to 82±21 uM. Additionally, there were increased concentrations of multiple odd chain saturated fatty acid forms among Group A dolphins throughout the modified diet compared to Month 0, including raised C15:0 and C17:0 neutral fatty acids (for example, triacylglycerides) and raised C15:0 and C17:0 phospholipids (for example, phosphatidylcholine and lysophosphatidylcholine) (Table 6). These changes in odd chain saturated fatty acid forms were not present in Group B control dolphins. Thus, approximate daily oral dosing of C15:0 at 28 mg/kg body weight or C17:0 at 7 mg/kg body weight may be used to achieve raised concentrations in these respective odd chain saturated fatty acids.

When the modified diet adding 50% mullet was fed to 20 Group A dolphins over 6 months, total serum concentrations of C26:0, a very long even chain saturated fatty acid, increased by Month 1 compared to Month 0 and maintained increased serum concentrations throughout the six months (Table 5). Additionally, there were increased concentrations of multiple additional very long even chain saturated fatty acid forms among Group A dolphins throughout the modified diet compared to Month 0, including raised serum C22:0 ceramide and hexosylceramide concentrations and raised C24:0 ceramide, dihydroceramide, and hexosylceramide concentrations (Table 6). These changes in very long even chain saturated fatty acid forms were not present in Group B control dolphins. The even chain saturated fatty acids, C16:0 and C18:0, either did not change or decreased among Group A dolphins while on the modified diet. Thus, approximate daily oral dosing of C24:0 at 1.9 mg/kg body weight may be used to achieve raised concentrations in very long even chain saturated fatty acids.

Figure 2A:
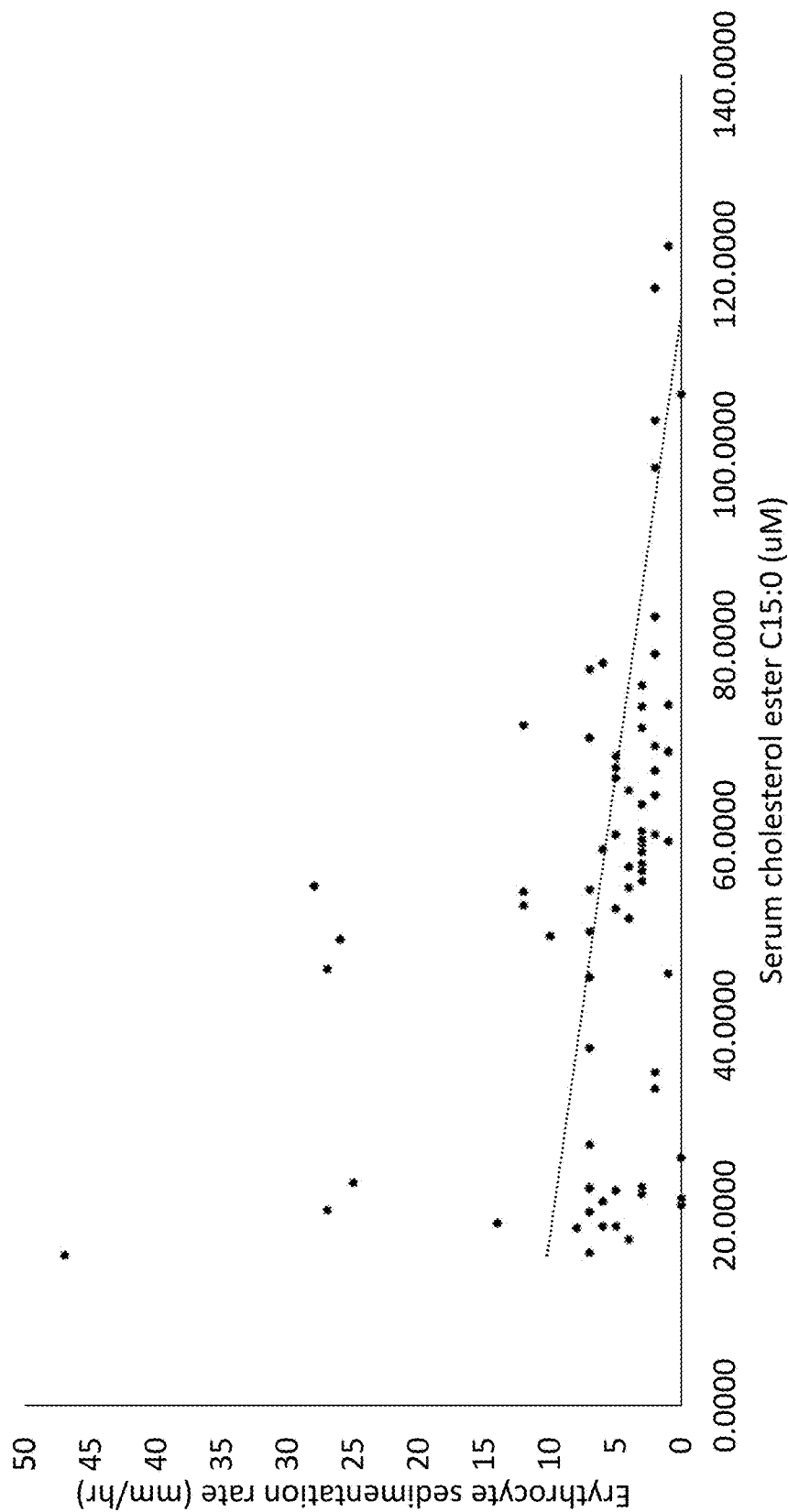
FIGS. 2A-2B provide data for inverse associations between serum concentrations of cholesterol ester C15:0 and phosphatidylcholine C17:0, with erythrocyte sedimentation rate, using simple linear regression models in dolphins on a modified fish diet.
Figure 2B:
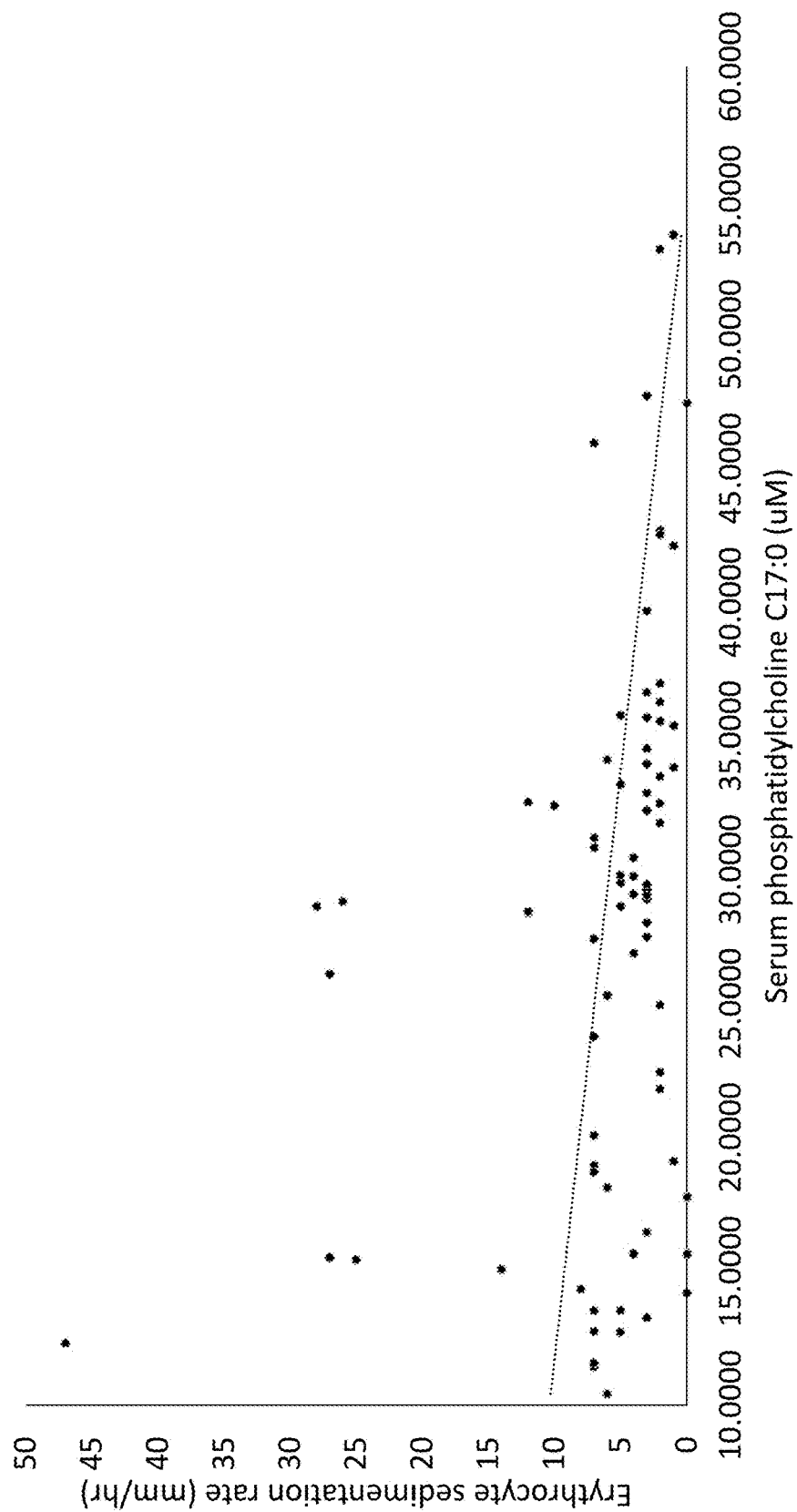

Increased serum concentrations of odd chain saturated fatty acids in Group A dolphins on the modified diet were independent, linear predictors of lowered erythrocyte sedimentation rate (Table 7). Specifically, increased serum concentrations of C15:0 cholesterol esters and C17:0 phosphatidylcholine independently predicted lower erythrocyte sedimentation rate. FIGS. 2A-2B demonstrate the linear associations between raised levels of these odd chain saturated fatty acid forms with lower erythrocyte sedimentation rate. These figures also reveal a threshold effect; namely, achieving serum cholesterol ester C15:0 concentrations greater than 60 uM or serum phosphatidylcholine C17:0 concentrations greater than 30 uM resulted in erythrocyte sedimentation rates lower than 15 mm/hr. Thus, raising serum concentrations of odd chain saturated fatty acids through increased daily oral intake of odd chain saturated fatty acids can improve inflammation. As shown in FIGS. 2A-2B, using a proposed therapeutic threshold of serum cholesterol ester C15:0 concentrations greater than 60 uM or serum phosphatidylcholine C17:0 concentrations greater than 30 uM may also maintain a lower erythrocyte sedimentation rate.

Figure 3A:
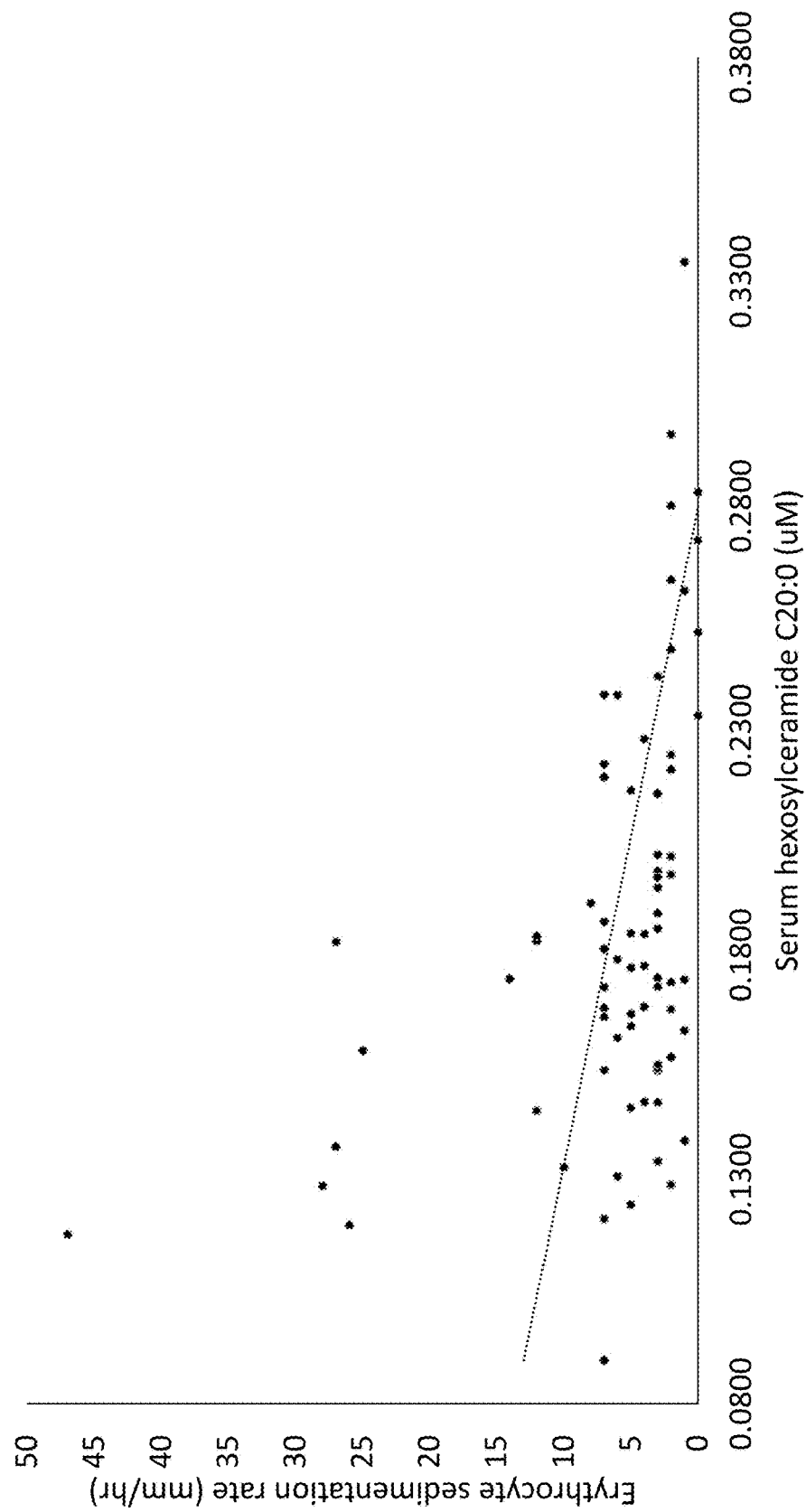
FIGS. 3A-3B provide data for inverse associations between serum concentrations of hexosylceramide forms of very long even chain saturated fatty acids (C20:0 and C22:0) with erythrocyte sedimentation rate, using simple linear regression models in dolphins on a modified fish diet.
Figure 3B:
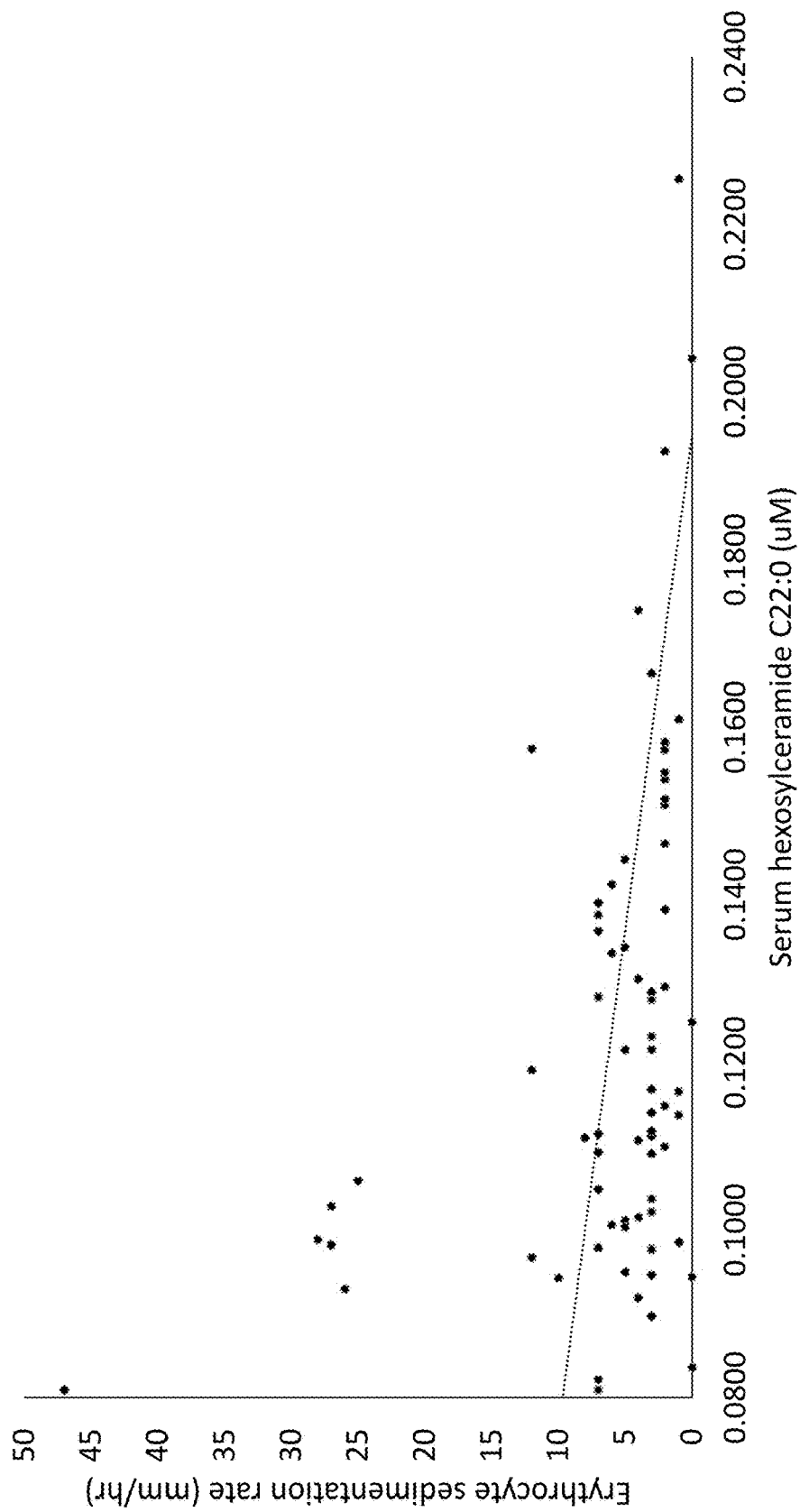
Figure 4A:
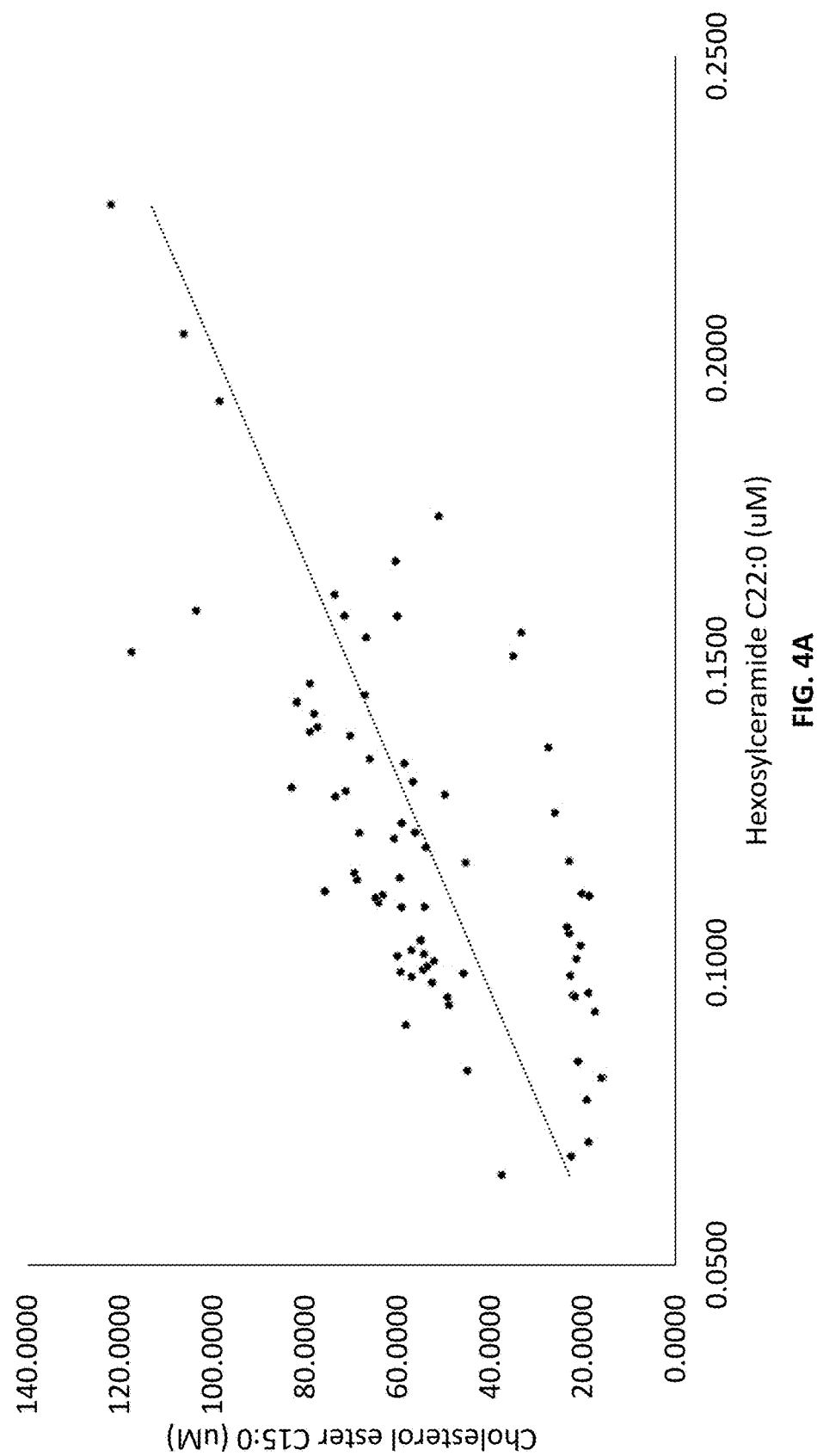
FIGS. 4A-4D provide data for positive associations between serum concentrations of cholesterol ester C15:0 and phosphatidylcholine C17:0 with hexosylceramide forms of very long even chain saturated fatty acids (C22:0 and C24:0), using simple linear regression models in dolphins on a modified fish diet.
Figure 4B:
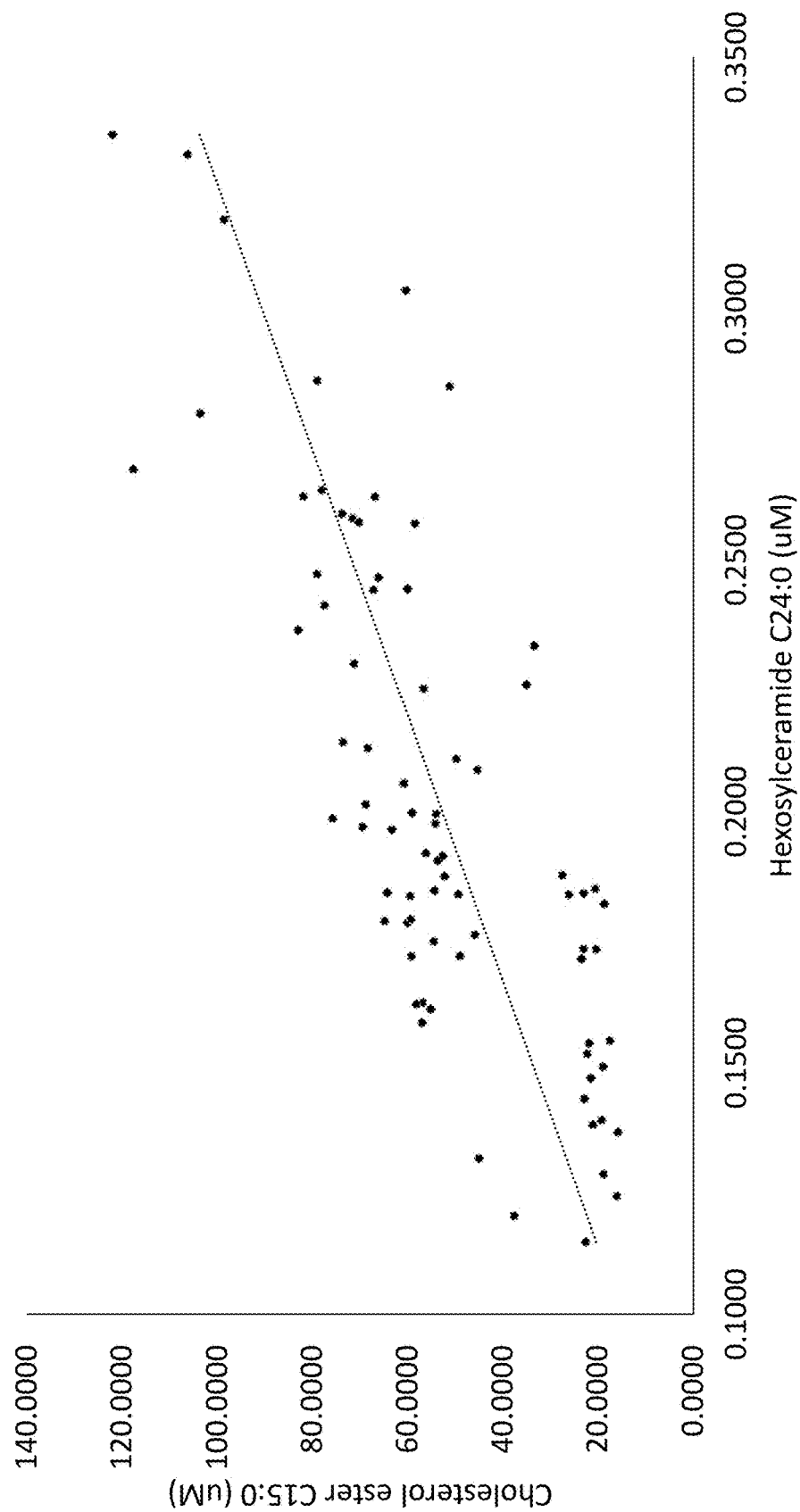
Figure 4C:
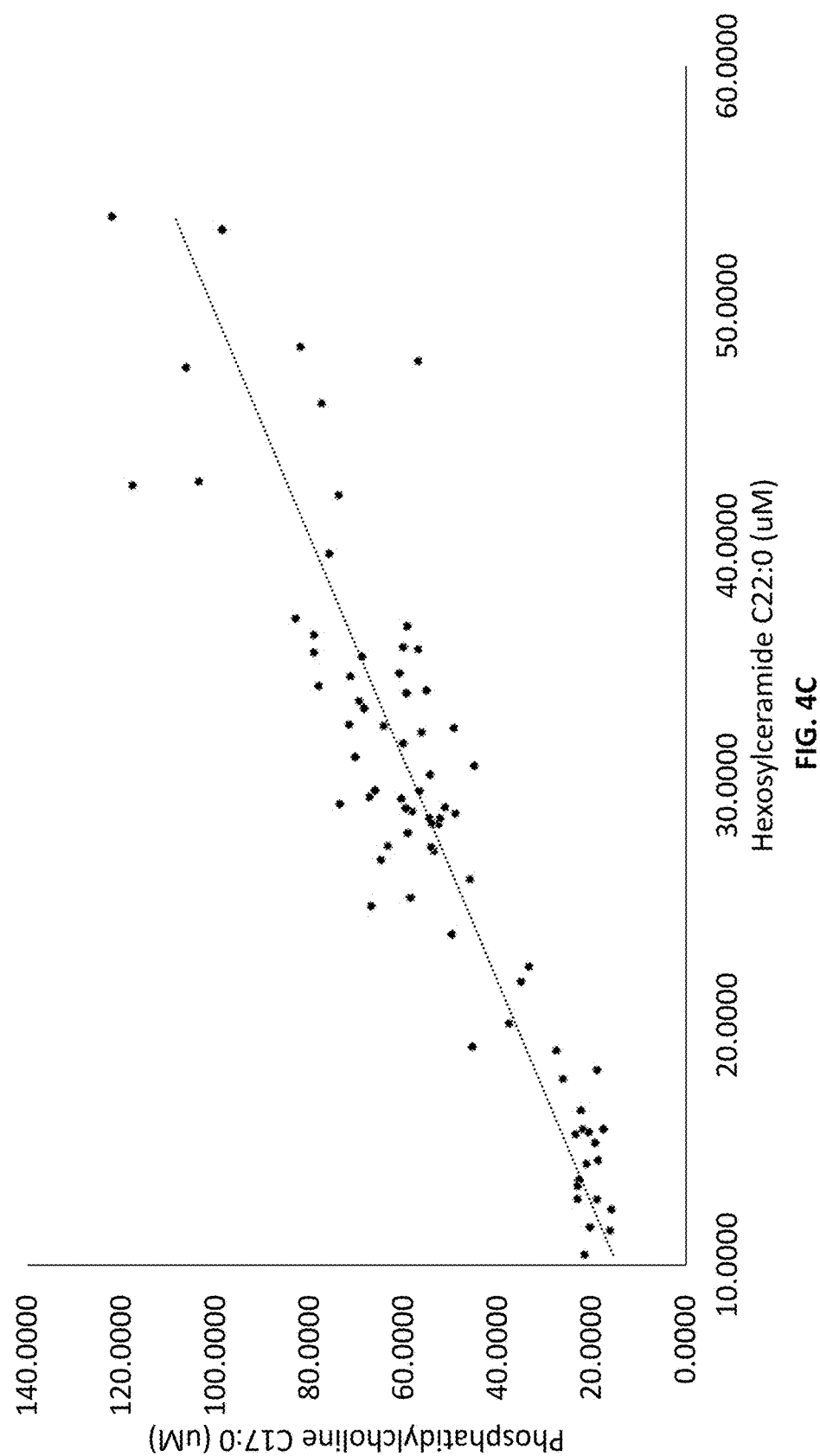
Figure 4D:
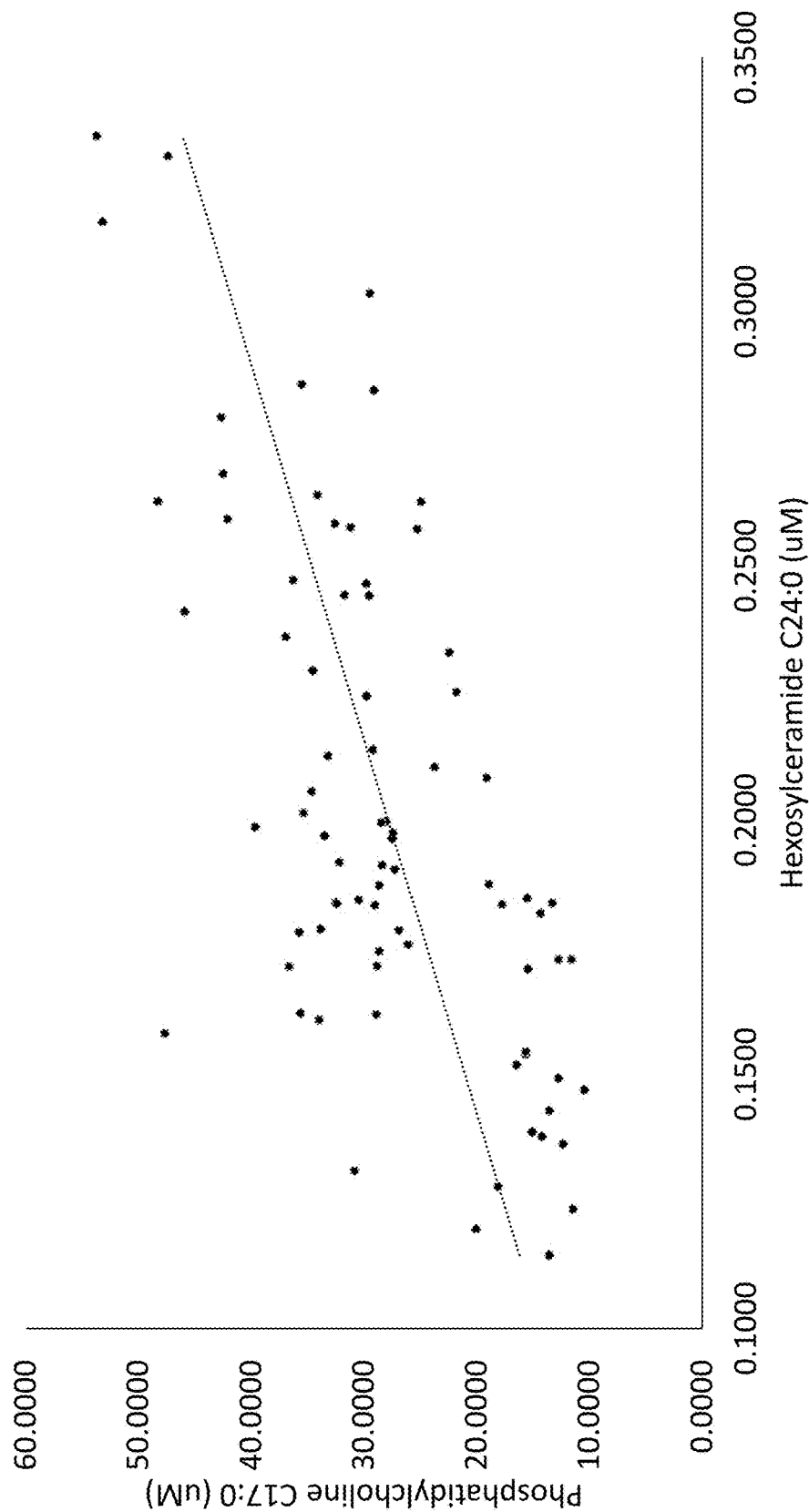

Increased serum concentrations of very long even chain saturated fatty acids in Group A dolphins on the modified diet were independent, linear predictors of improved red blood cell indices (in other words, anemia) (Table 7). Specifically, increased concentrations of C20:0 and C22:0 hexosylceramide forms independently predicted lower erythrocyte sedimentation rate. FIGS. 3A-3B demonstrate the linear associations between raised levels of these very long even chain saturated fatty acid forms with lower erythrocyte sedimentation rate. These figures also reveal a threshold effect; namely, achieving serum hexosylceramide C20:0 concentrations greater than 0.20 uM or serum hexosylceramide C22:0 concentrations greater than 0.11 uM resulted in erythrocyte sedimentation rates lower than 15 mm/hr. Thus, raising serum concentrations of very long even chain saturated fatty acids can improve red blood cell indices and alleviate anemia. As shown in FIGS. 3A-3B, using a proposed therapeutic threshold of serum hexosylceramide C20:0 concentrations greater than 0.20 uM or serum hexosylceramide C22:0 concentrations greater than 0.11 uM may also maintain a lower erythrocyte sedimentation rate.

Increased serum concentrations of odd chain saturated fatty acids that were independent predictors of improving anemia correlated with increased serum concentrations of very long even chain saturated fatty acids that were independent predictors of improving anemia. As demonstrated in FIGS. 4A-4D, increasing serum concentrations of C15:0 cholesterol ester forms had positive associations with increasing serum concentrations of C22:0 and C24:0 hexosylceramide forms. Increasing serum concentrations of C17:0 phosphatidylcholine forms had positives association with increasing serum concentrations of C22:0 and C24:0 hexosylceramide forms. Thus, increased serum concentrations of odd chain saturated fatty acid forms as a result of daily oral intake of odd chain saturated fatty acids are also associated with increases in serum concentrations of targeted very long even chain fatty acid forms.

Figure 5:
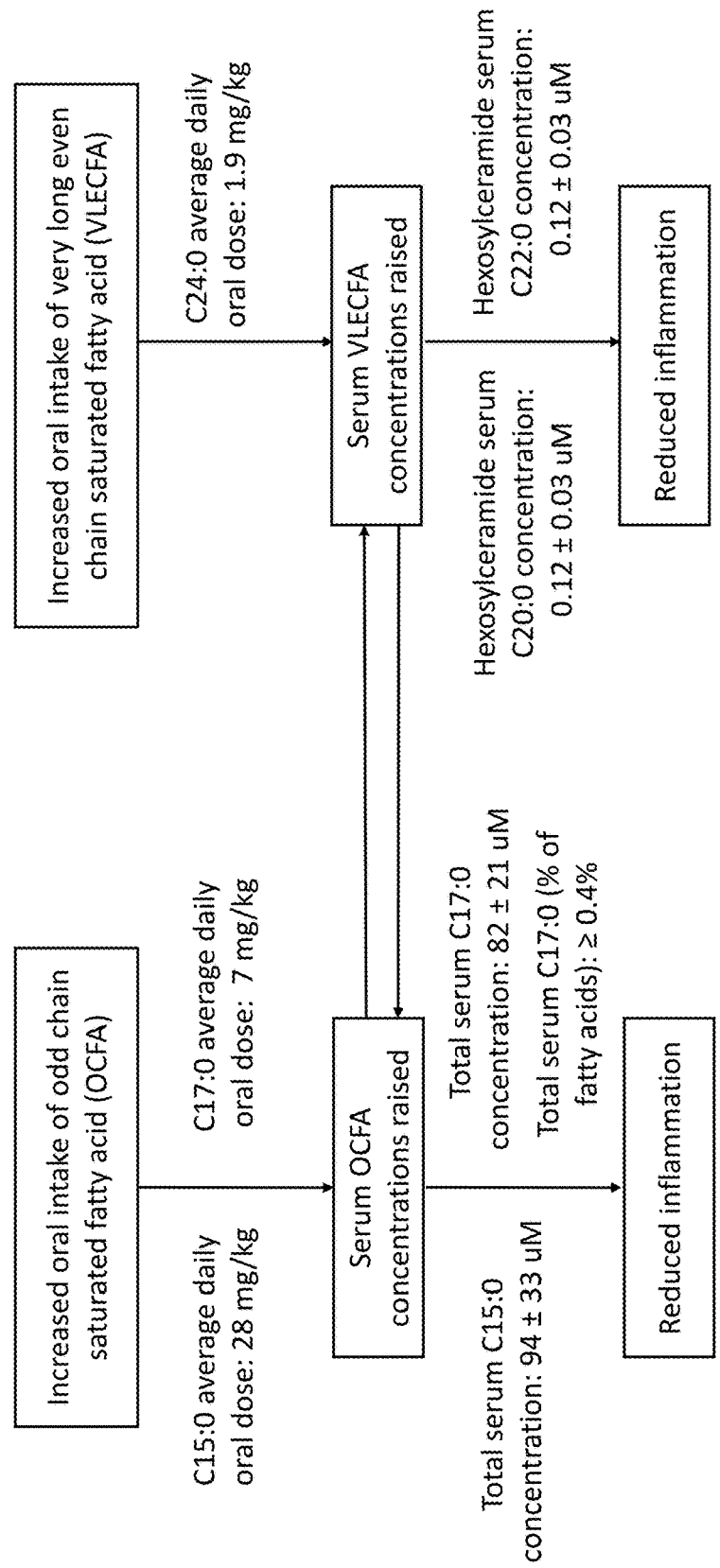
FIG. 5 provides a flow chart summarizing daily oral dosing of odd chain saturated fatty acids and very long even chain saturated fatty acids provided to dolphins and resultant serum fatty acid concentrations achieved that were predictive of lowered erythrocyte sedimentation rate and alleviated inflammation in dolphins on a modified fish diet.

FIG. 5 summarizes results from the dolphin study, including that 1) increased oral intake of odd chain saturated fatty acids results in increased serum concentrations of total odd chain saturated fatty acids and a variety of odd chain saturated fatty acid forms, 2) increased oral intake of very long even chain saturated fatty acids results in increased serum concentrations of very long even chain saturated fatty acid forms, 3) increased serum concentration of odd chain saturated fatty acids due to increased odd chain saturated fatty acid oral intake is associated with increased serum concentrations of very long even chain saturated fatty acid forms, and 4) increased serum concentrations of odd chain saturated fatty acids or very long even chain saturated fatty acids independently predict linear decreases in erythrocyte sedimentation rate and alleviated inflammation.

Sample Collection and Transport

Blood was collected into BD Vacutainer serum separator tubes (for serum fatty acid profiles) or an evacuated tube containing EDTA ($K_3$). Serum separator tubes were centrifuged at 3000 rpm for 10 minutes within 30 to 60 minutes of collection and chilled during processing until shipment. Serum was transferred to cryovials and stored at −80° C. until shipment on dry ice via overnight courier to the reference laboratories.

Sample Analysis

Total serum fatty acid profiles were performed by the Genetics Laboratories at the Kennedy Krieger Institute. Fatty acids were analyzed by capillary gas chromatography/mass spectrometry of pentaflourobenzyl bromide fatty acid derivatives using an AT-Silar-100 column (Grace, Columbia, Md. 21044) as previously described. Each run was required to pass clinical laboratory quality control before the data were released. CV % were typically under 10%. Percent fatty acids in serum was used as a sturdier index to help reduce potential variability in serum among study dolphins.

Determination of serum fatty acid concentrations, including a variety of fatty acid classes, were performed by Metabolon, Inc. (Durham, N.C.) using complex lipidomics. Lipids were extracted from samples using dichloromethane and methanol in a modified Bligh-Dyer extraction in the presence of internal standards with the lower, organic, phase being used for analysis. The extracts were concentrated under nitrogen and reconstituted in 0.25 mL of dichloromethane:methanol (50:50) containing 10 mM ammonium acetate. The extracts were placed in vials for infusion-MS analyses, performed on a SelexION equipped Sciex 5500 QTRAP using both positive and negative mode electrospray. Each sample was subjected to 2 analyses, with IMS-MS conditions optimized for lipid classes monitored in each analysis. The 5500 QTRAP was operated in MRM mode to monitor the transitions for over 1,100 lipids from up to 14 lipid classes. Individual lipid species were quantified based on the ratio of signal intensity for target compounds to the signal intensity for an assigned internal standard of known concentration. Lipid class concentrations were calculated from the sum of all molecular species within a class, and fatty acid compositions were determined by calculating the proportion of individual fatty acids within each class.

Fish fatty acid profiles were performed by Covance Laboratories (Madison, Wis. 53703). Each of the following fish types was mixed with water and homogenized for uniformity: capelin from Canada and Iceland (*Mallotus villosus*), herring (*Clupea harengus*), mackerel (*Scomber japonicus*), squid (*Loligo opalescens*), and striped mullet (*Mugil cephalus*). The lipid was extracted, saponified with 0.5N methanolic sodium hydroxide, and methylated with 14% BF3-methanol. The resulting methyl esters of the fatty acids were extracted with heptane. An internal standard was added prior to the lipid extraction. The methyl esters of the fatty acids were analyzed by gas chromatography using external standards for quantitation. These data were used to calculate total daily intake of each fatty acid for each study dolphin based upon recorded diets eaten, by fish type, for their 1) pre-study baseline diet, and 2) in-study modified (Group A) or baseline (Group B) diets.

A commercially available blood sedimentation system (that correlates with the Westergren method) was used to determine 60-minute erythrocyte sedimentation rates from 1 mL of whole blood containing EDTA. At the commercial laboratory, the Olympus AU600 (Olympus America Inc, Center Valley, Pa). was used for serum biochemical analyses, including alkaline phosphatase.

Statistical analyses were conducted using World Programming System software (World Programming Ltd., Hampshire, United Kingdom). Significance was defined as a P value less than or equal to 0.05. Mean daily dietary intake of individual fatty acids were compared between pre-study and in-study diets for Group A and Group B dolphins using Wilcoxon rank sum tests. Indices of inflammation (erythrocyte sedimentation rate and alkaline phosphatase) and serum fatty acid concentrations (total and individual classes) from Month 1, 3, and 6 were compared with Month 0 for Group A and Group B dolphins using repeated measures ANOVA (MIXED model). Fatty acids that had increased serum concentrations on the modified diet, and not in controls, were included in a stepwise regression model (for example, C17:0 total, triacylglyceride, phosphatidylcholine, lyso-phosphatidylcholine, phosphatidylethanolamine, and lyso-phosphatidylethanolamine forms were included in one model) to determine which forms were independent predictors of erythrocyte sedimentation rate. Fatty acids that were independent predictors of erythrocyte sedimentation rate were then tested for linear associations with erythrocyte sedimentation rate using simple linear regressions. Fatty acids that were independent predictors of erythrocyte sedimentation rate and had inverse linear associations with these indices (defined as a P value less than or equal to 0.05 and an $R^2$ greater than or equal to 0.1), were characterized as fatty acids that independently predicted improved inflammation.

Table 1 provides comparisons of red blood cell indices, serum total odd chain fatty acids (% of total fatty acids) and serum total very long even chain fatty acids (% of total fatty acids) between Navy Marine Mammal Program (MMP) dolphins and wild Sarasota Bay dolphins.

TABLE 1

| Blood variable | MMP Dolphins (n = 30) | Sarasota Bay Dolphins (n = 19) | P value |
|---|---|---|---|
| Serum fatty acid (%) | | | |
| Odd chain saturated fatty acids | | | |
| C15:0 | 0.3 ± 0.1 | 1.1 ± 0.4 | <0.0001 |
| C17:0 | 0.3 ± 0.1 | 1.3 ± 0.4 | <0.0001 |
| Very long even chain saturated fatty acids | | | |
| C20:0 | 0.9 ± 0.2 | 1.5 ± 0.3 | <0.0001 |
| C22:0 | 0.2 ± 0.04 | 0.7 ± 0.2 | <0.0001 |
| C24:0 | 0.1 ± 0.0 | 0.5 ± 0.1 | <0.0001 |

Table 2 provides comparisons of demographics between Group A dolphins placed on the modified fish diet and Group B dolphins maintained on the baseline diet.

TABLE 2

| Demographic | Group A dolphins on modified diet (n = 20) | Group B control dolphins remaining on baseline diet (n-10) | P value |
|---|---|---|---|
| Mean age (years) | 22 ± 14 | 26 ± 10 | 0.41 |
| Sex (no. and % female) | 9/20 (45%) | 4/10 (40%) | 0.79 |
| Body weight (lbs) | 389 ± 49 | 402 ± 45 | 0.33 |

Table 3 provides comparisons of total daily nutrient intake between baseline and study diets for Group

TABLE 3

|  | Case Dolphins | | Control Dolphins | |
| --- | --- | --- | --- | --- |
| Daily Nutrient Intake | Baseline diet (pre-study) | Modified diet | Baseline diet (pre-study) | Baseline diet (during study) |
| Total kilocalories | 8,923 ± 2,411 | 9,139 ± 2,171 | 8,442 ± 1,527 | 7,702 ± 2,897 |
| Total pounds | 16 ± 4 | 16 ± 4 | 15 ± 3 | 15 ± 3 |
| Total fat (g) | 494 ± 133 | 460 ± 111* | 468 ± 87 | 457 ± 89 |
| Total carbohydrates (g) | 25 ± 11 | 21 ± 5 | 20 ± 6 | 20 ± 6 |
| Fatty acids (g) | | | | |
| Odd chain saturated fatty acids | | | | |
| C15:0 | 1.3 ± 0.4 | 4.5 ± 1.1* | 1.2 ± 0.2 | 1.2 ± 0.3 |
| C17:0 | 0.3 ± 0.1 | 1.1 ± 0.3* | 0.3 ± 0.1 | 0.4 ± 0.2 |
| Even chain saturated fatty acids | | | | |
| C16:0 | 58 ± 17 | 48 ± 14* | 55 ± 9 | 53 ± 14 |
| C18:0 | 6.4 ± 1.9 | 7.6 ± 2.0 | 6.0 ± 0.9 | 6.1 ± 1.8 |
| Very long even chain saturated fatty acids | | | | |
| C20:0 | 0.8 ± 0.2 | 0.4 ± 0.1* | 0.7 ± 0.1 | 0.7 ± 0.2 |
| C22:0 | 0.1 ± 0.05 | 0.1 ± 0.04 | 0.1 ± 0.02 | 0.1 ± 0.1 |
| C24:0 | 0 | 0.3 ± 0.1* | 0 | 0 |
| Total omega 3 | 81 ± 23 | 60 ± 17* | 77 ± 12 | 75 ± 15 |
| Total polyunsaturated fats | 84 ± 24 | 64 ± 18* | 79 ± 13 | 77 ± 16 |
| Total saturated fats | 86 ± 25 | 73 ± 20* | 81 ± 13 | 78 ± 19 |
| Total fatty acids | 338 ± 99 | 236 ± 66* | 320 ± 53 | 305 ± 61 |

*$P \leq 0.05$ compared to baseline, pre-study diet

Table 4 provides comparisons of indicators of inflammation among Group A case dolphins on a modified diet and Group B control dolphin on a baseline diet.

TABLE 4

| Indicator of inflammation | Case dolphins fed modified diet (n = 20) | | | | Control dolphins maintained on baseline diet (n = 10) | | | |
| --- | --- | --- | --- | --- | --- | --- | --- | --- |
|  | Month 0 | Month 1 | Month 3 | Month 6 | Month 0 | Month 1 | Month 3 | Month 6 |
| Erythrocyte sedimentation rate | 10 ± 11 | 5 ± 6* | 4 ± 6* | 6 ± 6* | 3 ± 2 | 3 ± 2 | 4 ± 2 | 4 ± 2 |
| Alkaline phosphatase | 381 ± 165 | 360 ± 157 | 324 ± 163* | 285 ± 135* | 323 ± 183 | 329 ± 170 | 322 ± 149 | 311 ± 150 |

*$P \leq 0.05$

Table 5 provides comparisons of total serum fatty acid concentrations among Group A case dolphins on a modified diet and Group B control dolphin on a baseline diet.

TABLE 5

Total serum fatty acid concentration (uM)

| Fatty acids | Case dolphins fed modified diet (n = 20) | | | | Control dolphins maintained on baseline diet (n = 10) | | | |
| --- | --- | --- | --- | --- | --- | --- | --- | --- |
|  | Month 0 | Month 1 | Month 3 | Month 6 | Month 0 | Month 1 | Month 3 | Month 6 |
| Odd chain saturated fatty acids | | | | | | | | |
| C15:0 | 35 ± 9 | 94 ± 33* | 111 ± 29* | 101 ± 29* | 41 ± 19 | 45 ± 41 | 49 ± 19 | 38 ± 13 |
| C17:0 | 51 ± 9 | 82 ± 21* | 93 ± 23* | 85 ± 15* | 55 ± 17 | 53 ± 27 | 60 ± 9 | 50 ± 15 |
| Even chain saturated fatty acids | | | | | | | | |
| C14:0 | 243 ± 63 | 195 ± 50 | 226 ± 46 | 206 ± 33 | 253 ± 90 | 229 ± 114 | 294 ± 40 | 264 ± 92 |
| C16:0 | 1445 ± 194 | 1372 ± 199 | 1505 ± 221 | 1450 ± 155 | 1521 ± 368 | 1411 ± 426 | 1639 ± 165 | 1484 ± 371 |
| C18:0 | 1190 ± 229 | 1130 ± 188 | 1161 ± 194 | 1202 ± 140 | 1245 ± 348 | 1106 ± 379 | 1292 ± 184 | 1188 ± 344 |

TABLE 5-continued

Total serum fatty acid concentration (uM)

| Fatty acids | Case dolphins fed modified diet (n = 20) | | | | Control dolphins maintained on baseline diet (n = 10) | | | |
|---|---|---|---|---|---|---|---|---|
| | Month 0 | Month 1 | Month 3 | Month 6 | Month 0 | Month 1 | Month 3 | Month 6 |
| Very long even chain saturated fatty acids | | | | | | | | |
| C20:0 | 94 ± 22 | 87 ± 17 | 98 ± 17 | 96 ± 15 | 96 ± 27 | 84 ± 26 | 102 ± 14 | 91 ± 22 |
| C22:0 | 23 ± 4 | 21 ± 3 | 23 ± 3 | 24 ± 5 | 24 ± 5 | 21 ± 5 | 27 ± 5 | 23 ± 5 |
| C24:0 | 18 ± 3 | 17 ± 3 | 18 ± 3 | 18 ± 3 | 19 ± 4 | 17 ± 4 | 20 ± 4 | 20 ± 4 |
| C26:0 | 1.0 ± 0.1 | 0.8 ± 0.1* | 0.9 ± 0.1* | 0.9 ± 0.1* | 1.1 ± 0.2 | 1.0 ± 0.2 | 1.1 ± 0.2 | 1.1 ± 0.2 |

*$P \leq 0.05$

Table 6 provides comparisons of various serum fatty acid form concentrations with significant ($P \leq 0.05$) changes from Month 0 in Group A case dolphins on a modified diet. These changes were not present in Group B control dolphin on a baseline diet (not shown).

TABLE 6

| Fatty acids | Serum concentrations (uM) with significant changes from Month 0 in case dolphins fed modified diet (n = 20) | | | |
|---|---|---|---|---|
| | Month 0 | Month 1 | Month 3 | Month 6 |
| Odd chain saturated fatty acids C15:0 | | | | |
| FFA | 3.8 ± 1.3 | 4.2 ± 1.5 | 3.6 ± 0.8 | 3.8 ± 1.3 |
| CE | 22 ± 5 | 61 ± 19 | 66 ± 17 | 64 ± 22 |
| TAG | 5.5 ± 1.9 | 11 ± 5 | 16 ± 10 | 12 ± 7 |
| PC | 5.4 ± 1.8 | 19 ± 8 | 22 ± 7 | 19 ± 7 |
| LPC | 0.91 ± 0.20 | 2.8 ± 0.9 | 2.9 ± 0.8 | 3.0 ± 1.1 |
| C17:0 | | | | |
| CE | 14 ± 4 | 18 ± 7 | 20 ± 8 | 21 ± 9 |
| TAG | 6.6 ± 2.1 | 11 ± 5 | 16 ± 10 | 11 ± 5 |
| PC | 15 ± 3 | 32 ± 9 | 34 ± 8 | 31 ± 7 |
| LPC | 1.8 ± 0.4 | 3.9 ± 0.8 | 3.8 ± 0.8 | 3.9 ± 1.1 |
| PE | 1.3 ± 0.2 | 1.6 ± 0.6 | 1.9 ± 0.6 | 1.4 ± 0.2 |
| LPE | 0.04 ± 0.01 | 0.09 ± 0.02 | 0.09 ± 0.02 | 0.09 ± 0.02 |
| Even chain saturated fatty acids C14:0 | | | | |
| CE | 126 ± 32 | 86 ± 21 | 93 ± 20 | 92 ± 25 |
| C16:0 | | | | |
| CE | 273 ± 50 | 226 ± 41 | 244 ± 33 | 245 ± 48 |
| CER | 0.28 ± 0.04 | 0.24 ± 0.04 | 0.25 ± 0.05 | 0.23 ± 0.03 |
| HCER | 0.52 ± 0.12 | 0.41 ± 0.09 | 0.44 ± 0.09 | 0.43 ± 0.11 |
| SPM | 126 ± 29 | 105 ± 20 | 112 ± 20 | 105 ± 23 |
| C18:0 | | | | |
| CER | 0.59 ± 0.20 | 0.39 ± 0.12 | 0.46 ± 0.18 | 0.40 ± 0.14 |
| DCER | 0.16 ± 0.05 | 0.10 ± 0.03 | 0.12 ± 0.05 | 0.11 ± 0.04 |
| Very long even chain saturated fatty acids C20:0 | | | | |
| FFA | 6.6 ± 2.5 | 4.4 ± 1.4 | 5.0 ± 2.3 | 17 ± 10 |
| LPC | 0.36 ± 0.08 | 0.27 ± 0.05 | 0.27 ± 0.07 | 0.31 ± 0.09 |
| CER | 0.50 ± 0.10 | 0.39 ± 0.08 | 0.42 ± 0.08 | 0.41 ± 0.07 |
| HCER | 0.04 ± 0.01 | 0.03 ± 0.01 | 0.03 ± 0.01 | 0.03 ± 0.01 |
| C22:0 | | | | |
| CE | 8.5 ± 2.4 | 5.7 ± 1.5 | 5.9 ± 1.5 | 6.3 ± 2.1 |
| CER | 0.19 ± 0.04 | 0.23 ± 0.05 | 0.26 ± 0.07 | 0.25 ± 0.06 |
| HCER | 0.10 ± 0.02 | 0.12 ± 0.03 | 0.13 ± 0.03 | 0.13 ± 0.03 |
| C24:0 | | | | |
| CER | 0.38 ± 0.11 | 0.65 ± 0.17 | 0.75 ± 0.28 | 0.68 ± 0.19 |
| DCER | 0.07 ± 0.02 | 0.11 ± 0.03 | 0.13 ± 0.05 | 0.12 ± 0.03 |
| HCER | 0.16 ± 0.03 | 0.21 ± 0.05 | 0.22 ± 0.05 | 0.22 ± 0.05 |

FFA = free fatty acid,
CE = cholesterol ester,
TAG = triacylglyceride,
PC = phosphatidylcholine,
LPC = lysophosphatidylcholine,
PE = phosphatidylethanolamine,
LPE = lysophosphatidylethanolamine,
CER = ceramide,
DCER = dihydroceramide,
HCER = hexosylceramide Table 7 provides raised serum fatty acids that were independent, linear predictors of lowered erythrocyte sedimentation rate in Group A dolphins while on a modified diet.

TABLE 7

| Serum fatty acid and form | P value for fatty acid serum concentration as independent, linear predictor of erythrocyte sedimentation rate |
|---|---|
| Odd chain saturated fatty acid C15:0 | |
| Cholesterol ester | 0.004 (−) |
| C17:0 | |
| Phosphatidylcholine | <0.0001 (−) |
| Very long even chain saturated fatty acid C20:0 | |
| Hexosylceramide | 0.0003 (−) |
| C22:0 | |
| Hexosylceramide | 0.004 (−) |

Raised serum concentrations of odd chain saturated fatty acids and very long even chain saturated fatty acids are independent, linear predictors of lowered erythrocyte sedimentation rate and alkaline phosphatase, two indicators of inflammation. When dolphins with inflammation increased their dietary intake of odd chain saturated fatty acids and very long even chain saturated fatty acids by changing fish types fed, their erythrocyte sedimentation rates and alkaline phosphatase levels lowered, reflecting alleviated inflammation. This suggests how odd chain saturated fatty acid and very long even chain saturated fatty acid deficiencies may be underlying and treatable causes of inflammation and subsequent chronic diseases in humans. This may be because bottlenose dolphins (Tursiops truncatus) and humans are large-brained, long lived species that develop similar diseases, including conditions associated with abnormal metabolism and aging. As such, dolphins have emerged as valuable animal models relevant to human health.

Several parallels have been identified between dolphins and humans. For example, dolphins and humans are long-lived. The average lifespan of dolphin is 20 years in the wild and 32 years at the MMP, with the maximum lifespan being approximately 60 years. Shared long lifespans between dolphins and humans are improving knowledge of chronic and aging-associated diseases in humans, including inflammation. Additionally, dolphins and humans have large brains. Among mammals, humans have the highest encephalization quotient (EQ=7.4), defined as the actual versus expected brain size given a species' body size. Second to humans is the bottlenose dolphin (EQ=5.3), higher than the chimpanzee (EQ=2.4) and much higher than the mouse (EQ=0.5). Similar to humans, positron emission tomography scans of living dolphins have revealed high levels of glucose consumption by the dolphin brain. As such, shared large brain size and associated high demand for glucose are likely drivers for common glucose metabolism and associated conditions in dolphins and humans.

Dolphins and humans have similar glucose transport systems, as well as common genetic adaptations associated with glucose metabolism. Adult dolphins have a high capacity for red blood cell glucose transport using the GLUT-1 transporter isoform; previous to this discovery, this capability was thought to be limited to primates. Common red blood cell glucose transport systems in cetaceans and primates are believed to be due to high central nervous system glucose demands. Also, the dolphin genome has been partially sequenced by Baylor University, based upon a dolphin at the U.S. Navy Marine Mammal Program. Dolphins have genetic evolutionary adaptations that are unique to long-lived, large brained species, including humans and elephants. Further, dolphins and humans have similar genes responsible for glucose metabolism (Office of Naval Research funded study, unpublished). Accordingly, Dolphins are appropriate models for human inflammation, metabolic syndrome, hyperferritinemia, and related conditions.

Dolphins and Humans Develop Similar Diseases and Disease Complications

Similar to humans, common bottlenose dolphins (Tursiops truncatus) can develop inflammation, including elevated erythrocyte sedimentation rate, alkaline phosphatase, and ceruloplasmin, as well as increased haptoglobin associated with higher glucose. Dolphins managed at the Navy Marine Mammal Program living in San Diego Bay, Calif., are a well-studied population with regard to metabolism, and this group has higher insulin, triglycerides, ferritin, and iron compared to a wild bottlenose dolphin group living in Sarasota Bay, Fla. Importantly, the presence of case and reference populations of dolphins for metabolic syndrome and inflammation parallel similar human population comparisons.

Similar to people, dolphins can develop nonalcoholic fatty liver disease (NAFLD). NAFLD has been found in both wild and managed collection dolphins, supporting that dolphins have general physiologic susceptibilities to metabolic syndrome. NAFLD is associated with inflammation in humans and dolphins, and progresses to hepatitis and cirrhosis. Progression of these metabolic perturbations with chronic, low level inflammation in both species is associated with insulin resistance and worsened glucose control.

Similar to humans, dolphins can develop a chronic condition involving high ferritin (hyperferritinemia) and iron. This disease in humans and dolphins involves excessive iron deposition primarily in the liver's Kupffer cells, progression with age, and associations with inflammation, elevated lipids, insulin, and liver enzymes. This metabolic state in dolphins is associated with neither mutations in the HFE gene.

Dolphins develop similar age-associated blood changes as aging humans. Specifically, absolute lymphocytes, serum globulins, and mean platelet volume increase linearly with increasing old age (=aging from 30 up to 50 years old). Mean white blood cells, neutrophils, serum globulins, erythrocyte sedimentation rates, serum cholesterol, and serum triglycerides; and the prevalence of neutrophilic leukocytosis, hyperglobulinemia, and hypercholesterolemia, were more likely to be higher as geriatric dolphins got older. This study demonstrated that older dolphins have changes in hematological and serum chemistry values similar to those found in older humans, including the presence of inflammation. As such, bottlenose dolphins can serve as a useful comparative model for aging in humans.

For the above reasons, dolphins and humans share important common ground related to anatomy, physiology, and disease states that support the dolphin as an important and relevant animal model for human diseases, including inflammation. The results cited herein for dolphins can also be beneficial for humans.

Example 2

In humans, obesity, aging, cardiometabolic diseases, and dementia, including Alzheimer's disease, are associated with inflammation, including elevation of the adipokines (cytokines), interleukin 6 (IL-6), interleukin 18 (IL-18), and monocyte chemoattractant protein-1 (MCP-1) (References attached, Targher et. al). Following the results from EXAMPLE 1, it can be hypothesized that oral administration of a synthetic odd chain saturated fatty acid would lower inflammation in a traditional laboratory animal model.

This study examined the impact of daily oral administration of synthetic pentadecanoic acid (C15:0) on inflammation in an obese mouse model. Twenty C57BL/6J mice were fed a high fat diet (HFD) (D12492, 60% kcals fat) for 8 weeks. Study mice were then divided into the following two groups of ten: vehicle controls and C15:0-treated (5 mg/kg body weight). The predicted therapeutic dose of 5 mg/kg was based upon modified diet studies in the dolphin model. The test article was a synthetic powder form stable at room temperature and purchased from Sigma-Aldrich (Products W433400 (≥99% C15:0). The test article was provided daily via gastric gavage for 12 weeks (84 days) while continuing ad libitum access to the HFD. Body weight and food intake were measured weekly. Serum IL-6, IL-18, and MCP-1 levels were measured at Day 84. Data from the treated group were compared to the control group using Wilcoxon rank sum analyses. Significance was defined as a P value less than or equal to 0.05.

Mice in the C15:0 treatment group tolerated the test article throughout the study. There were no early mortalities among mice in the treated group; one mouse in the control group had an unscheduled death on Week 7. No changes were found in body weight, percent body weight change, or food intake when comparing the study groups (not shown).

Figure 6A:
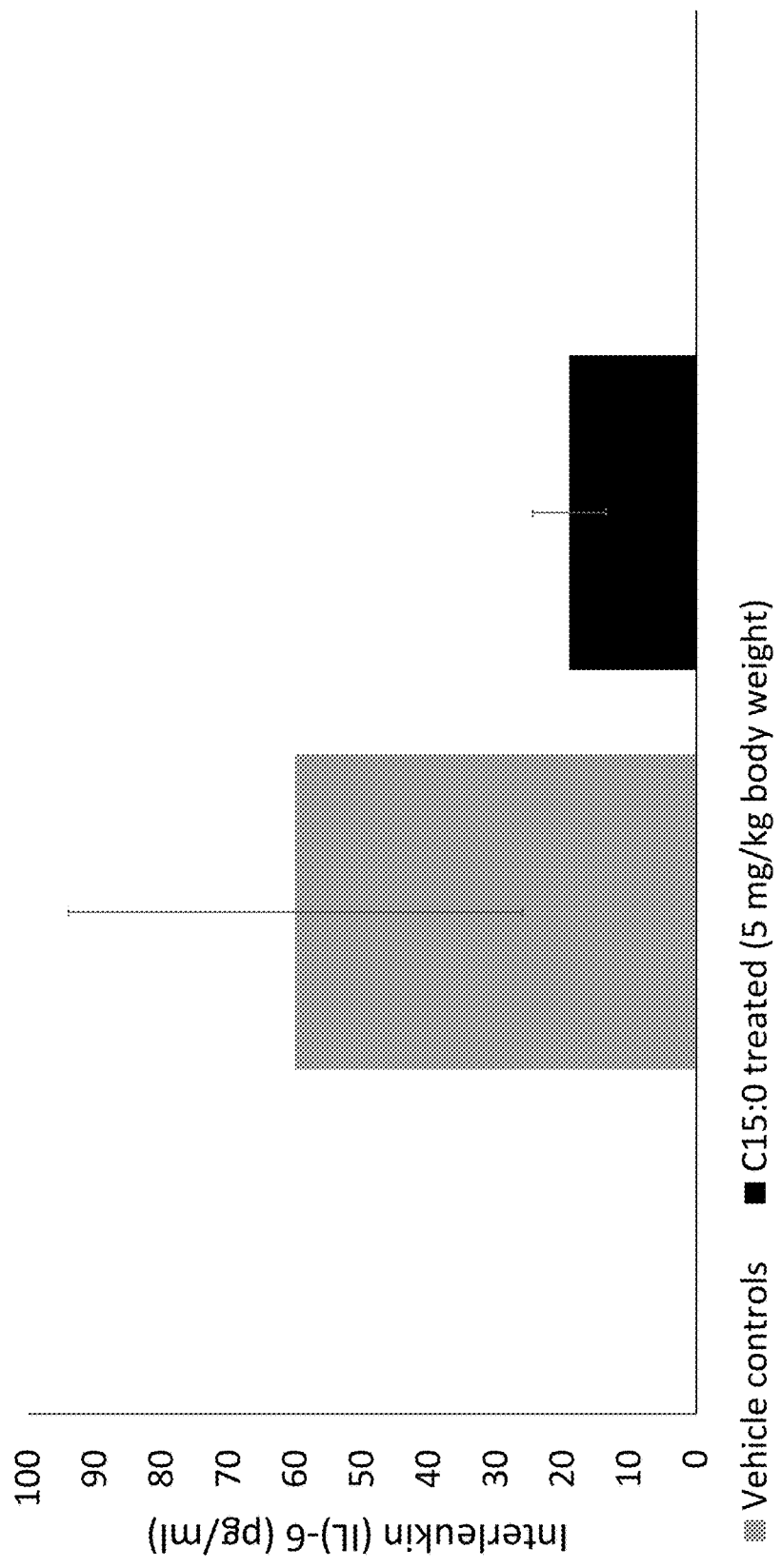
FIGS. 6A-6C provide data for the chronic anti-inflammatory effect of daily oral synthetic C15:0 after 12 weeks of treating high fat diet induced obese mice; specifically, cytokines interleukin 6 (IL-6), interleukin 18 (IL-18), and monocyte chemoattractant protein-1 (MCP-1), also called chemokine (C-C motif) ligand 2 (CCL2) were all reduced compared to vehicle controls.
Figure 6B:
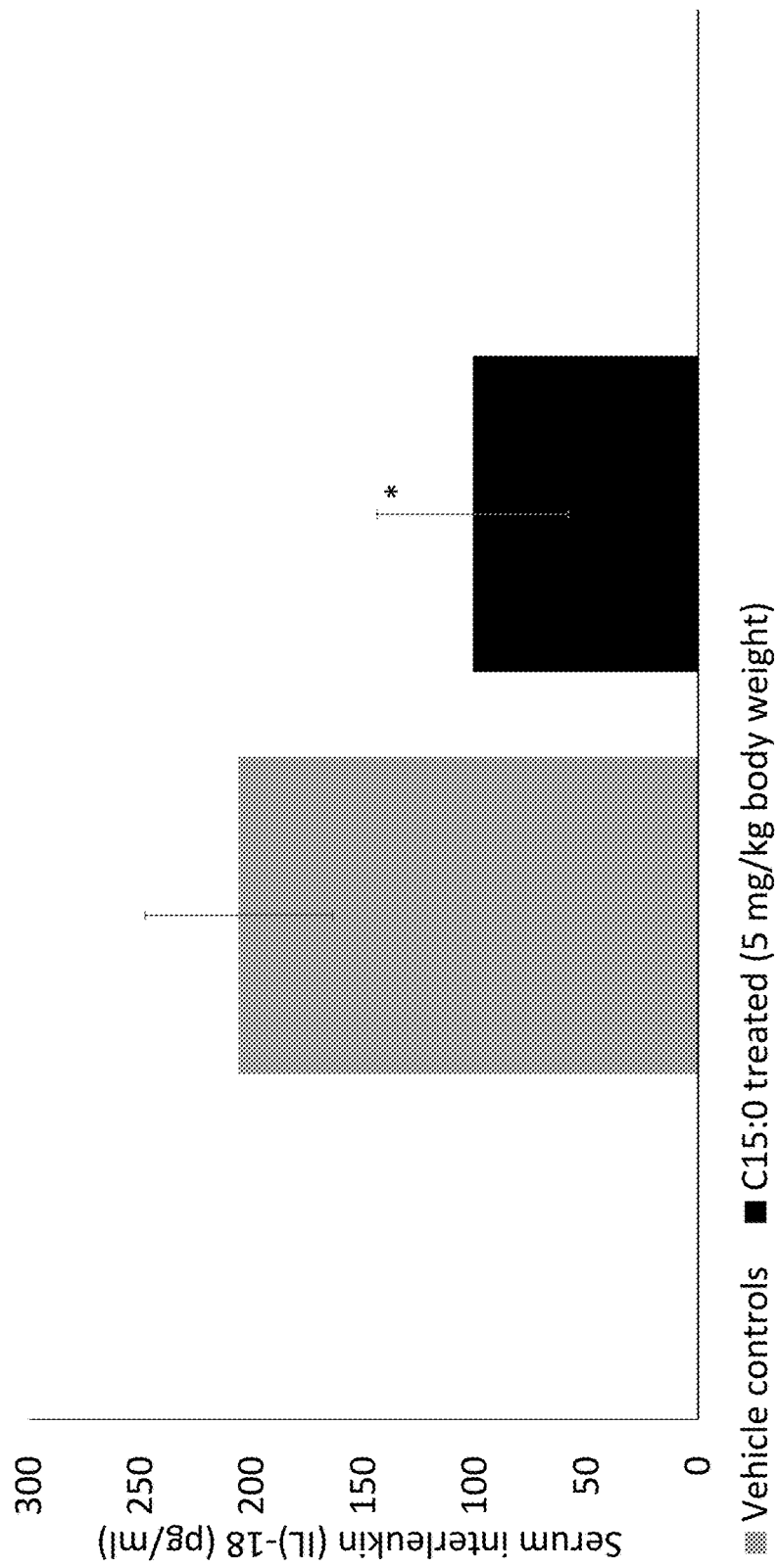
Figure 6C:
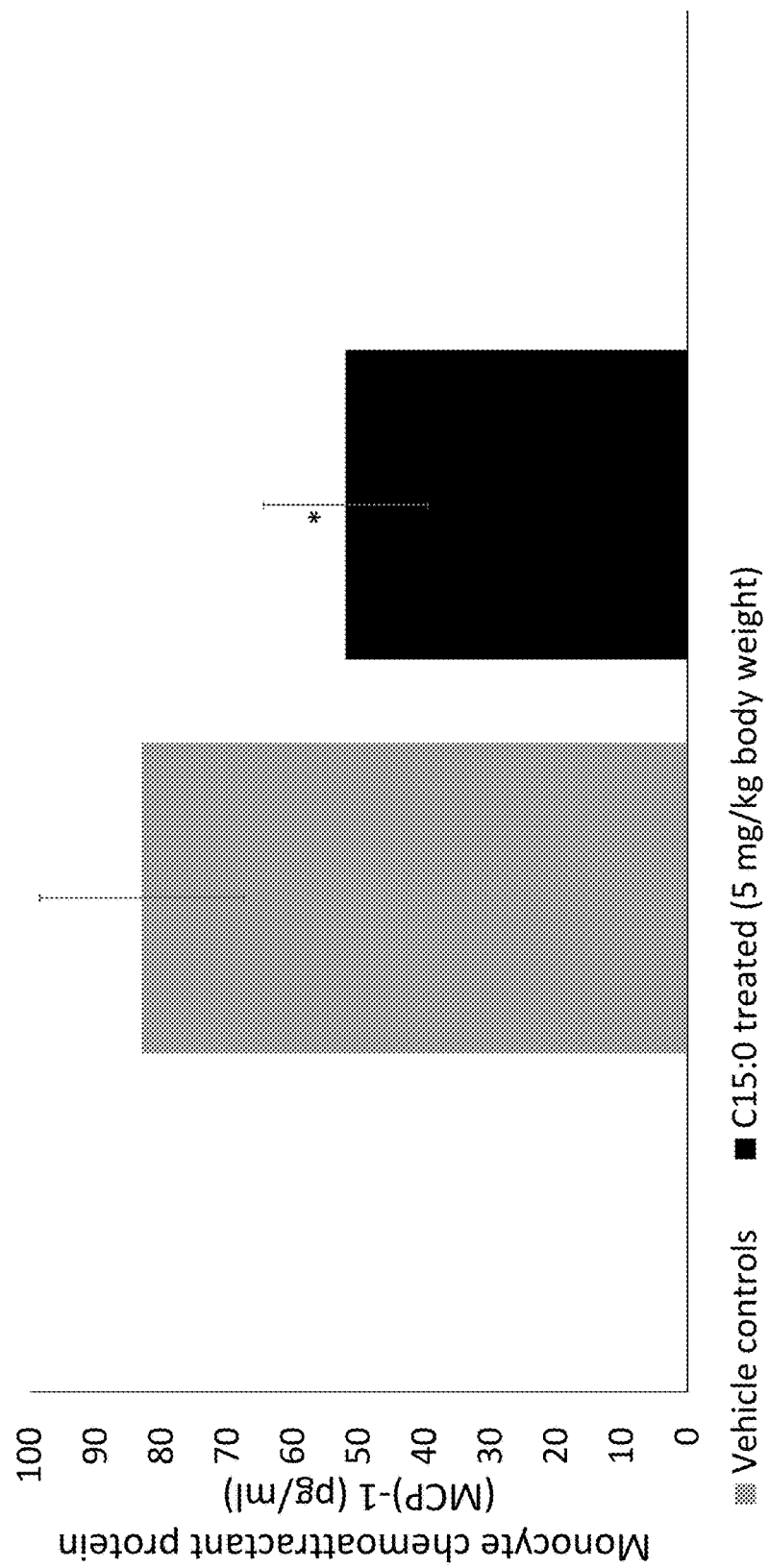

When comparing the C15:0 treatment group with the vehicle control group, subjects treated with C15:0 (5 mg/kg) had lower inflammation and adipokines (IL-6, IL-18, and MCP-1) compared to controls (Table 8, FIGS. 6A-6C).

Table 8 provides comparisons of serum adipokine (cytokines) levels between obese mice treated with oral synthetic C15:0 for 84 days and vehicle controls.

TABLE 8

| Adipokine | Vehicle control (n = 10) | C15:0 5 mg/kg dose (n = 10) |
|---|---|---|
| IL-6 | 60 ± 68 | 19 ± 11* |
| IL-18 | 206 ± 84 | 101 ± 86* |
| MCP-1 | 83 ± 31 | 52 ± 25* |

*$P \leq 0.05$

Odd chain fatty acids (heptadecanoic acid, or C17:0, and pentadecanoic acid, or C15:0) are saturated fatty acids present in ruminant whole fat dairy products. Odd chain saturated fatty acids are assembled by bacteria in the rumen and pass from the rumen to the milk. When off the shelf dairy products were tested in the current study, odd chain saturated fatty acids were highest in butter and whole fat yogurt and absent in nonfat dairy products. Interestingly, despite consumer's movement away from high fat foods, dairy consumption in humans has been associated with multiple health benefits, including lower markers of inflammation and lower risks of insulin resistance syndrome, metabolic syndrome, and type 2 diabetes. To date, the mechanism of the benefits of dairy products on human inflammation and metabolism has not been determined. Based upon the results using the methods of the embodiments, it can be proposed that odd chain saturated fatty acids may be key players in the anti-inflammatory benefits of dairy products in humans.

To take advantage of these benefits, odd chain saturated fatty acids can be used in acid in a supplement, food additive, food fortifier, beverage additive, beverage fortifier, or pharmaceutical in any form, including as a tablet, encapsulated pill, gelcap pill, liquid suspension, spray, and powder. Additionally, diagnostic tests and assays for odd chain saturated fatty acids in human and animal samples (including blood (serum, plasma, and erythrocyte membranes), urine, and feces) can be used to detect low odd chain saturated fatty acids and to continually monitor odd chain saturated fatty acids levels in patients. The use of odd chain saturated fatty acids can prevent, stem, and treat: 1) Elevated erythrocyte sedimentation rate, other biomarkers of inflammation, and associated complications, including anemia of chronic disease, insulin resistance, metabolic syndrome, hypertension, diabetes, nonalcoholic fatty liver disease, cardiovascular disease, cancer, diseases of aging, neurodegenerative diseases, including Alzheimer's disease and other forms of dementia, and other related conditions. These egregious health effects can be prevented not only in dolphins, but because of the similarities in blood panels, they can be prevented in human mammals as well.

The data suggest a direct effect for odd chain saturated fatty acids and very long even chain saturated fatty acids on alleviating inflammation in the feeding study involved fish with higher odd chain saturated fatty acids and very long even chain saturated fatty acids. The potential impact (or cumulative impacts) of other nutrients in the modified diet on serum ferritin has not been determined. Identification of 1) higher concentrations of odd chain saturated fatty acids and very long even chain saturated fatty acids as independent predictors of lower serum erythrocyte sedimentation rate, 2) demonstrated increased dietary intake and concentration of odd chain saturated fatty acids and very long even chain saturated fatty acids during the feeding study, and 3) coincident decreases in erythrocyte sedimentation rates and alkaline phosphatase and increases in serum concentrations of odd chain saturated fatty acids and very long even chain saturated fatty acids by month 1 that were not present among controls, provide evidence that increasing dietary odd chain saturated fatty acids and very long even chain saturated fatty acids contributed to decreased erythrocyte sedimentation rates and alkaline phosphatase, which indicates that odd chain saturated fatty acids and very long even chain saturated fatty acids can be used to treat inflammation, as well as other associated or related conditions.

Odd chain saturated fatty acids and very long even chain saturated fatty acids deficiencies can be used to detect a risk of or cause for inflammation. Dietary supplementation with odd chain saturated fatty acids and very long even chain saturated fatty acids can help resolve inflammation and associated diseases.

The following materials are incorporated herein by reference in the entirety: Colegrove K. (2015) Histomorphology of the bottlenose dolphin (*Tursiops truncatus*) pancreas and association of increasing islet β-cell size with chronic hypercholesterolemia. J Gen Comp Endocrinol 14:17-23; Venn-Watson (2012) Hemochromatosis and fatty change: building evidence for insulin resistance in bottlenose dolphins (*Tursiops truncatus*). J Zoo Wildlf Med 43:S35-S47; Venn-Watson S. (2007) Big brains and blood glucose: Common ground for diabetes mellitus in humans and healthy dolphins. Comp Med 57:390-5; Venn-Watson S. (2013) Blood-Based Indicators of Insulin Resistance and Metabolic Syndrome in Bottlenose Dolphins (*Tursiops truncatus*). Front Endocrinol (Lausanne) 4:136; Venn-Watson S. (2011) Dolphins as animal models for type 2 diabetes: Sustained, postprandial hyperglycemia and hyperinsulinemia. Gen Comp Endocrin 170:193-9; Venn-Watson S. (2014) Dolphins and Diabetes: Applying One Health for breakthrough discoveries. Front Endocrinol DOI 10.3389/fendo.2014.00227; Venn-Watson S. (2015) Increased dietary intake of saturated fatty acid heptadecanoic acid (C17:0) associated with decreasing ferritin and alleviated metabolic syndrome in dolphins. PLOS ONE 10:e0132117. Sobolesky P M, Harrell T, Parry C, Venn-Watson S, Janech M G (2016) Feeding a modified diet to bottlenose dolphins leads to an increase in serum adiponectin and sphingolipids consistent with improved insulin sensitivity. Front Endocrinol 7:33; Venn-Watson S, Carlin K, Andrews G A, Chavey P S, Mazzaro L (2013) Associations of ceruloplasmin and haptoglobin with inflammation and glucose in bottlenose dolphins (*Tursiops truncatus*) J Comp Clin Path DOI: 10.1007/s00580-013-1738-0. Venn-Watson S, Smith C R, Gomez F, Jensen E D (2011) Physiology of aging among healthy, older bottlenose dolphins (*Tursiops truncatus*): comparisons with aging humans. *J Comp Phys B* 181:667-680.

Methods and compositions related to or applicable to inflammation or related conditions are discussed in the following references, which are incorporated by reference herein in their entirety Blood 88:3608-3614; Zandman- Goddard G, Shoenfeld Y (2008) Hyperferritinemia in autoimmunity. IMAJ 10: 83-84; Zandman-Goddard G, Shoenfeld Y (2008) Ferritin in autoimmune diseases. Autoimmunity Rev 6:457-463; Hodson, L, Skeaff C M, Fielding B A. (2008) A review of even-chain fatty acid metabolism and the role of arachidic acid (C20:0) and lignoceric acid (C24:0) in health and disease, The Lipid Handbook, 605-633; Yin, G. (2015) Pfeuffer M, Jaudszus A, Pentadecanoic and Heptadecanoic Acids: Multifacted Odd-Chain Fatty Acids, Adv Nutr. 2016 Jul. 15; 7(4):730-4; Fave, G. (2004) Physiochemical properties of lipids: new strategies to manage fatty acid bioavailability. Cell Bol Biol 50:815-831. Ramirez, M. (2001) Absorption and distribution of dietary fatty acids from different sources. Early Hum Develop 65:S95-S101; Craik J (1998) GLUT-1 mediation of rapid glucose transport in dolphin (*Tursiops truncatus*) red blood cells. Am J Physiol 274:R112-R9; McGowen M. (2012) Dolphin genome provides evidence for adaptive evolution of nervous system genes and a molecular rate slowdown. Royal Society Proc B 279:3643-51; Jenkins B. (2015) A review of odd-chain fatty acid metabolism and the role of pentadecanoic acid (C15:0) and heptadecanoic acid (C17:0) in health and disease. Molecules 20:2425-44; Mansson H L (2008) Fatty acids in bovine milk fat. Food Nutr Res 52:4; Magnusdottir O K. (2014) Plasma alkylresorcinols C17:0/C21:0 ratio, a biomarker of relative whole-grain rye intake, is associated to insulin sensitivity: a randomized study. Eur J Clin Nutr 68:453-458; Luzia L A. (2013) The influence of season on the lipid profiles of five commercially important species of Brazilian fish. Food Chem 83:93-97; Benatar J R. (2014) The effects of changing dairy intake on trans and saturated fatty acid levels—results from a randomized controlled study. Nutr J 13:32; Abdullah M M. (2015) Recommended dairy product intake modulates circulating fatty acid profile in healthy adults: a multi-centre cross-over study. Br J Nutr 113:435-44; Forouhi N. (2014) Differences in the prospective association between individual plasma phospholipid saturated fatty acids and incident type 2 diabetes: the EPIC-InterAct case-cohort study. Lancet Diabetes Endocrinol 2:810-8; Patel P. (2010) Fatty acids measured in plasma and erythrocyte-membrane phospholipids and derived by food-frequency questionnaire and the risk of new-onset type 2 diabetes: a pilot study in the European Prospective Investigation into Cancer and Nutrition (EPIC)-Norfolk cohort. Am J Clin Nutrition 92:1214-22; Krachler B. (2008) Fatty acid profile of the erythrocyte membrane preceding development of Type 2 diabetes mellitus. Nutrition, metabolism, and cardiovascular diseases. NMCD 18:503-10; Maruyama C. (2008) Differences in serum phospholipid fatty acid compositions and estimated desaturase activities between Japanese men with and without metabolic syndrome. J Atherscler Thromb 15:306-313; Choi H. (2005) Dairy consumption and risk of type 2 diabetes mellitus in men: a prospective study. JAMA Internal Med 165:997-1003; Kratz M. (2014) Dairy fat intake is associated with glucose tolerance, hepatic and systemic insulin sensitivity, and liver fat but not beta-cell function in humans. The American journal of clinical nutrition. 99:1385-96; Mennen L. (2000) Possible protective effect of bread and dairy products on the risk of the metabolic syndrome. Nutrition Research 20:335-47; Pereira M. (2002) Dairy consumption, obesity, and the insulin resistance syndrome in young adults: the CARDIA study. JAMA 287:2081-9; Sandrou D. (2000) Low-fat/calorie foods: current state and perspectives. Crit Rev Food Sci Nutr 40:427-47; Pfeuffer M. (2006) Milk and the metabolic syndrome. Obesity Rev 8:109-18; Ruidavets J B. (2007) High consumptions of grain, fish, dairy products and combinations of these are associated with a low prevalence of metabolic syndrome. J Epidemiol Community Health 61:810-817. PMID: 17699537; Gibson R A (1983) Australian fish—an excellent source of both arachidonic acid and n-3 polyunsaturated fatty acids. Lipids 18:743-752; Glauber H. (1988) Adverse metabolic effect of omega-3 fatty acids in non-insulin-dependent diabetes mellitus. Ann Int Med 108:663-668. PMID: 3282462; Popp-Snijders C. (1987) Dietary supplementation of omega-3 polyunsaturated fatty acids improve insulin sensitivity in non-insulin-dependent diabetes. Diabetes Res 4:141-147. PMID: 3038454; Wells R S. (2013) Evaluation of potential protective factors against metabolic syndrome in bottlenose dolphins: feeding and activity patterns of dolphins in Sarasota Bay, Fla. Frontiers Endo 4:139; Ellervik C. (2001) Prevalence of hereditary haemochromatosis in late-onset type 1 diabetes mellitus: a retrospective study. Lancet 358:1405-1409. PMID: 11705485; Wells R S. (2004) Bottlenose dolphins as marine ecosystem sentinels: developing a health monitoring system. EcoHealth 1:246-254; Barros N B. (1998) Prey and feeding patterns of resident bottlenose dolphins (*Tursiops truncatus*) in Sarasota Bay, Fla. J Mammal 79:1045-1059; Berens-McCabe E. (2010) Prey selection in a resident common bottlenose dolphin (*Tursiops truncatus*) community in Sarasota Bay, Fla. Marine Biol 157:931-942; Lagerstedt S A. (2001) Quantitative determination of plasma C8-C26 total fatty acids for the biochemical diagnosis of nutritional and metabolic disorders. Mol Gen Metabol 73:38-45; Anderson A J C (1954) Margarine. London. Pergamon Press; Mansson H L (2008) Fatty acids in bovine milk fat. Food Nutr Res 52:4; Fernandes R. (2013) Relationship between acute phase proteins and serum fatty acid composition in morbidly obese patients. Dis Markers 35:104-102; Forouhi N G. (2014) Differences in the prospective association between individual plasma phospholipid saturated fatty acids and incident type 2 diabetes: the EPIC-InterAct case-cohort study. Lancet Diabetes Endocrinol 2:810-818. doi: 10.1016/S2213-8587(14)70146-9 PMID: 25107467; Benatar J R. (2014) The effects of changing dairy intake on trans and saturated fatty acid levels—results from a randomized controlled study. Nutr J 13:32. doi: 10.1186/1475-2891-13-32 PMID: 24708591; Slifka K A. (2013) Comparative diet analysis of fish species commonly consumed by managed and free-ranging bottlenose dolphins (*Tursiops truncatus*). Int J Vet Med 10:1; Ozogul Y. (2007) Fatty acid profiles and fat contents of commercially important seawater and freshwater fish species of Turkey: A comparative study. Food Chem 103:217-223; Suresh Y. (2001) Protective action of arachidonic acid against alloxan-induced cytotoxicity and *diabetes mellitus*. Prostaglan Leuko Essent Fatty Acids 64:37-53; Venn-Watson S. (2015) Adrenal gland and lung lesions in Gulf of Mexico common bottlenose dolphins (*Tursiops truncatus*) found dead following the Deepwater Horizon oil spill. PLOS ONE 10(5):e0126538. doi: 10.1371/journal.pone.0126538 PMID: 25992681; Venn-Watson S. (2015) Annual survival, mortality, and longevity of bottlenose dolphins (*Tursiops truncatus*) at the U.S. Navy Marine Mammal Program, 2004-2013. J Am Vet Med 246:893-898; Venn-Watson S. (2008) Clinical relevance of elevated transaminases in a bottlenose dolphin (*Tursiops truncatus*) population. J Wildlf Dis 44:318-330; Akbar, H.. (2015). Alterations in Hepatic FGF21, Co-Regulated Genes, and Upstream Metabolic Genes in Response to Nutrition, Ketosis and Inflammation in Peripartal Holstein Cows. PLoS One 10, e0139963. doi: 10.1371/journal.pone.0139963; Annual, seasonal and individual variation in hematology and clinical blood chemistry profiles in bottlenose dolphins (*Tursiops*

*truncatus*) from Sarasota Bay, Fla. Comp Biochem Physiol A Mol Integr Physiol 148, 266-277. doi: 10.1016/j.cbpa.2007.04.017; Hannun, Y. A.. (2008). Principles of bioactive lipid signalling: lessons from sphingolipids. Nat Rev Mol Cell Biol 9, 139-150. doi: 10.1038/nrm2329; Hassanali, Z.. (2010). Dietary supplementation of n-3 PUFA reduces weight gain and improves postprandial lipaemia and the associated inflammatory response in the obese JCR:LA-cp rat. Diabetes Obes Metab 12, 139-147. doi: 10.1111/j.1463-1326.2009.01130.x; Profenno L A, Porsteinsson A P, Faraone S V (2010) Meta-analysis of Alzheimer's disease risk with obesity, diabetes, and related disorders. Biol Psych 67:505-512; Di Paolo G, Kim T W (2011) Linking lipids to Alzheimer's disease: cholesterol and beyond. Nature Rev Neurosci 12; Stephenson D, Perry D, Carillo M C, Sperling R, Katz R, Berry D et al. (2015) Building a roadmap for developing combination therapies for Alzheimer's disease. Expert Rev Neurother 15:327-333; Heneka M T, Carson M J, Khoury J E, Landreth G E, Brosseron F, Feinstein D L, et al. (2015) Neuroinflammation in Alzheimer's disease. Lancet Neurol 14:388-405; Ahmad R, Al-Mass A, Al-Ghawas D, Shareif N, Zghoul N, Melhem M, Hasan A, Al-Ghimlas F, Dermime S, Behbehani K (2013) Interaction of osteopontin with IL-18 in obese individuals: implications for insulin resistance. PLOS ONE 8: e63944; Bettcher B M, Fitch R, Wynn M J, Lalli M A, Elofson J, Jastrzab L, et al. (2016) MCP-1 and eotaxin-1 selectively and negatively associate with memory in MCI and Alzheimer's disease dementia phenotypes. Alz Dement: Diag Assess Dis Monit 3:91-97; Bossu P, Ciaramella A, Salani F, Bizzoni F, Varsi E, Iolio F D et al. (2008) Interleukin-18 produced by peripheral blood cells is increased in Alzheimer's disease and correlates with cognitive impairment. Brain, Behav, Immun 22:487-492; Dursun E, Gezen-Ak D, Hanagasi H, Bilgic B, Lohmann E, Ertan S, et al. (2015) The interleukin 1 alpha, interleukin 1 beta, interleukin 6 and alpha-2-macroglobin serum levels in patients with early or late onset Alzheimer's disease, mild cognitive impairment or Parkinson's disease. J Neuroinflamm 283: 50-57; Holmes C, Cunningham C, Zotova E, Woolford J, Dean C, Kerr S, Culliford D, Perry V H (2009) Systemic inflammation and disease progression in Alzheimer disease. Neurology 73:768-774; Kanda H, Tateya S, Tamori Y, Kotani K, Hiasa KI, Kitazawa R, Kitazawa S, Miyahi H, Maeda S, Egashira K, Kasuga M (2006) MCP-1 contributes to macrophage infiltration into adipose tissue, insuin resistance, and hepatic steatosis in obesity. J Clin Invest 116:1494-1505; T. Kiyota, M. Yamamoto, H. Xiong, M. P. Lambert, W. L. Klein, H. E. Gendeiman, et al. CCL2 accelerates microglia-mediated Abeta oligomer formation and progression of neurocognitive dysfunction PLoS One, 4 (2009), p. e6197; Martin-Jimenez C A, Gaitan-Vaca D M, Echeverria V, Gonzalez J (2016) Relationship between obesity, Alzheimer's disease, an Parkinson's disease: an astrocentric view. Mol Neurobiol. DOI: 10.1007/s12035-016-0193-8; McGeer P L, Rogers J, McGeer E G (2016) Inflammation, anti-inflammatory agents, and Alzheimer's disease: the last 22 years. J Alz Dis 54:853-857; Ojala J, Alafuzoff I, Herukka S K, van Groen T, Tanila H, Pierttila T (2009) Expression of interleukin-18 is increased in the brains of Alzheimer's disease patients. Neurobiol Aging 30:198-209; Panee J (2012) Monocyte chemoattractant protein 1 (MCP-1) in obesity and diabetes. Cytokine 60:1-12; Perry V H (2010) Contribution of systemic inflammation to chronic neurodegeneration. Acta Neuropathol 120:2770286; J. Ross, S. Sharma, J. Winston, M. Nunez, G. Bottini, M. Franceschi, et al. CHF5074 reduces biomarkers of neuroinflammation in patients with mild cognitive impairment: a 12-week, double-blind, placebo-controlled study Curr Alzheimer Res, 10 (2013), pp. 742-753; Salameh T S, Rhea E M, Banks W A, Hanson A J (2016) Insulin resistance, dyslipidemia, and apolipoprotein E interactions as mechanisms in cognitive impairment and Alzheimer's disease. Exp Biol Med doi: 10.1177/1535370216660770; Sindhu S, Thomas R, Shihab P, Sriraman D, Behbehani K, Ahmad R (2015) Obesity is a positive modulator of IL-6R and IL-6 expression in subcutaneous adipose tissue: significance for metabolic inflammation. PLOS ONE; Spyridaki E C, Avfoustinaki P D, Margioris A N (2016) Obesity, inflammation and cognition. Curr Opin Behav Sci 9:169-175; Tucsek Z, Toth P, Sosnowska D, Gautam T, Mitschelen M, Koller A, Szalai G, Sonntag W E, Ungvari Z, Csiszar A (2013) Obesity in aging exacerbates blood-brain barrier disruption, neuroinflammation, and oxidative stress in the mouse hippocampus: effects on expression of genes involved in beta-amyloid generation and Alzheimer's disease. 69:1212-1226; Van Eldik L J, Carrillo M C, Cole P E, Feuerbach D, Greenberg B D, Hendrix J A, et al. (2016) The roles of inflammation and immune mechanisms in Alzheimer's disease. Alz Demen: Transl Res Clin Intery 2:99-109; Wu Y Y, Hsu J L, Wang H C, Wu S J, Hong C J, Cheng I H J (2015) Alterations of the neuroinflammatory markers IL-6 and TRAIL in Alzheimer's disease. Dement Geriat Cogn Disord Extra 5:424-434.

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and "one or more' to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

I claim:

1. A method of treatment of inflammation, comprising: administering to a patient in need thereof a composition comprising an effective amount of at least one odd-chain saturated fatty acid, or pharmaceutically acceptable salts thereof, wherein the at least one odd-chain saturated fatty acid is selected from the group consisting of C15:0, C17:0, and combinations thereof.

2. The method of claim 1, wherein the at least one odd-chain saturated fatty acid or pharmaceutically acceptable salts thereof is provided as a pharmaceutical composition in a unit dosage form comprising the at least one odd-chain saturated fatty acid or pharmaceutically acceptable salts thereof and a pharmaceutically acceptable carrier.

3. The method of any one of claims 1 through 2, wherein the unit dosage form comprises from 0.01 mg to 10000 mg of the at least one odd-chain saturated fatty acid or pharmaceutically acceptable salts thereof.

4. The method of any one of claims 1 through 3, wherein the at least one odd chain saturated fatty acids is heptadecanoic acid or pentadecanoic acid.

5. The method of any one of claims 1 through 4, wherein the pharmaceutical composition is substantially free from even chain saturated fatty acids.

6. The method of any one of claims 1 through 5, wherein the pharmaceutical composition comprises a plurality of different odd-chain saturated fatty acids.

7. The method of any one of claims 1 through 5 or 6, wherein from 2.5 mg to 11 mg of the at least one odd-chain saturated fatty acid or pharmaceutically acceptable salts thereof is administered to the patient, per 1 kg of body weight, per day.

8. The method of any one of claims 1 through 5 or 6-7, wherein the at least one odd-chain saturated fatty acid or pharmaceutically acceptable salts thereof is administered to the patient once per day.

9. The method of any one of claims 1 through 5 or 6-8, wherein a serum concentration or a red blood cell membrane concentration of the at least one odd-chain saturated fatty acid is increased by at least about $0.001 \times 10^{-4}$ M above a pretreatment value.

10. The method of treatment of claim 1, wherein the composition further comprises an effective amount of at least one even-chain saturated fatty acid, wherein the at least one even-chain saturated fatty acid is selected from the group consisting of C16:0, C18:0, and combinations thereof.

11. The method of treatment of claim 1, wherein the composition further comprises an effective amount of at least one very long even chain saturated fatty acid, wherein the at least one very long even chain saturated fatty acid is selected from the group consisting of C20:0, C:22:0, and C24:0, and combinations thereof.

12. The method of treatment of claim 10, wherein the composition further comprises an effective amount of at least one very long even chain saturated fatty acid, wherein the at least one very long even chain saturated fatty acid is selected from the group consisting of C20:0, C:22:0, and C24:0, and combinations thereof.

* * * * *